US012564951B2

(12) United States Patent
Xi et al.

(10) Patent No.: US 12,564,951 B2
(45) Date of Patent: Mar. 3, 2026

(54) DISINFECTION ROBOTS

(71) Applicant: VERSITECH LIMITED, Hong Kong (CN)

(72) Inventors: Ning Xi, Hong Kong (CN); Ye Ma, Hong Kong (CN); Siyu Wang, Hong Kong (CN); Qingyang Wang, Hong Kong (CN); Jiajie Ye, Hong Kong (CN); Chun Kwok, Hong Kong (CN); Sheng Bi, Guangzhou (CN)

(73) Assignee: VERSITECH LIMITED, Hong Kong (CN)

( * ) Notice: Subject to any disclaimer, the term of this patent is extended or adjusted under 35 U.S.C. 154(b) by 459 days.

(21) Appl. No.: 17/969,850

(22) Filed: Oct. 20, 2022

(65) Prior Publication Data

US 2023/0126179 A1     Apr. 27, 2023

Related U.S. Application Data

(60) Provisional application No. 63/270,246, filed on Oct. 21, 2021.

(51) Int. Cl.
    *B25J 9/16*        (2006.01)
    *A61L 2/10*        (2006.01)
    (Continued)

(52) U.S. Cl.
    CPC .............. *B25J 9/1664* (2013.01); *A61L 2/10* (2013.01); *A61L 2/24* (2013.01); *B25J 5/007* (2013.01);
    (Continued)

(58) Field of Classification Search
    CPC ........ B25J 9/1664; B25J 5/007; B25J 9/1607; B25J 9/1633; B25J 11/0085; B25J 13/006;
    (Continued)

(56) References Cited

U.S. PATENT DOCUMENTS 4,925,312 A * 5/1990 Onaga .................... B25J 9/1633
                                                   318/568.22
6,456,901 B1 * 9/2002 Jindong
                    (Continued)

FOREIGN PATENT DOCUMENTS

CN        103619567 A * 3/2014    ............ B25J 13/085
CN        110125927 A * 8/2019
                    (Continued)

OTHER PUBLICATIONS

Neeltje van Doremalen, James O. Lloyd-Smith, Vincent J. Munster, Aerosol and surface stability of HCoV-19 (SARS-CoV-2) compared to SARS-CoV-19, medRxiv preprint https://doi.org/10.1101/2020.03.09.20033217, Mar. 9, 2020.
                    (Continued)

*Primary Examiner* — Sihar A Karwan
(74) *Attorney, Agent, or Firm* — Leason Ellis LLP

(57) ABSTRACT

A UV based surface disinfection system that consists of the UV light source, a robot arm, and an omni directional mobile base. The mobile robot can be programmed autonomously and be able to bring the UV light source to the centimeters away from surfaces to achieve effective and efficient surface disinfection. The mobile robot can navigate autonomously in a complicated environment to perform disinfection operation in a large area.

14 Claims, 23 Drawing Sheets
(14 of 23 Drawing Sheet(s) Filed in Color)

(51) Int. Cl.

| | |
|---|---|
| *A61L 2/24* | (2006.01) |
| *B25J 5/00* | (2006.01) |
| *B25J 11/00* | (2006.01) |
| *B25J 13/00* | (2006.01) |
| *B25J 13/08* | (2006.01) |
| *B25J 19/02* | (2006.01) |

(52) U.S. Cl.

CPC .......... *B25J 9/1607* (2013.01); *B25J 9/1633* (2013.01); *B25J 11/0085* (2013.01); *B25J 13/006* (2013.01); *B25J 13/089* (2013.01); *B25J 19/02* (2013.01); *A61L 2202/14* (2013.01); *A61L 2202/16* (2013.01)

(58) Field of Classification Search

CPC . B25J 13/089; B25J 19/02; A61L 2/10; A61L 2/24; A61L 2202/14; A61L 2202/16

USPC ......................................................... 700/245

See application file for complete search history.

(56) References Cited

U.S. PATENT DOCUMENTS

| | | | | |
|---|---|---|---|---|
| 2007/0078566 | A1* | 4/2007 | Wang ..................... | A61B 34/70 700/259 |
| 2014/0330452 | A1* | 11/2014 | Stewart ................... | B25J 19/02 701/2 |
| 2016/0271803 | A1* | 9/2016 | Stewart ................ | B25J 11/0085 |
| 2018/0064833 | A1* | 3/2018 | Childress .............. | B64D 11/02 |
| 2019/0389078 | A1* | 12/2019 | Bartlett ................... | B25J 5/007 |
| 2020/0147798 | A1* | 5/2020 | Toris ...................... | B25J 9/1682 |

FOREIGN PATENT DOCUMENTS

| | | | | | |
|---|---|---|---|---|---|
| CN | 113554559 | A | * | 10/2021 | ........... B25J 9/1605 |
| CN | 114102575 | A | * | 3/2022 | |
| CN | 112828862 | B | * | 9/2022 | ........... A61B 34/37 |
| DE | 102021109717 | A1 | * | 10/2021 | |
| JP | 2020192628 | A | * | 12/2020 | ........... B25J 13/006 |
| WO | WO-2014145471 | A1 | * | 9/2014 | ........ B29Q 17/2233 |

OTHER PUBLICATIONS

Samuel K. Moore, Flight of the GermFalcon: How a Potential Coronavirus-Killing Airplane Sterilizer Was Born, IEEE Spectrum, Mar. 9, 2020.

Theun de Groot, Anuradha Chowdhary, Jacques F. Meis, Andreas Voss, Killing of Candida auris by UV-C: Importance of exposure time and distance, Mycoses, 2019; 62(5), pp. 408-412.

Evan Ackerman, Autonomous Robots Are Helping Kill Corona virus in Hospitals, IEEE Spectrum, Mar. 11, 2020.

* cited by examiner

0: world frame
1: base frame
2: arm platform frame
3: joint1 frame
4: joint2 frame
5: joint3 frame
6: end-effector frame L.R.F. - Local Reference Frame
W.R.F - World Reference Frame
E.E.F - End Effector Frame

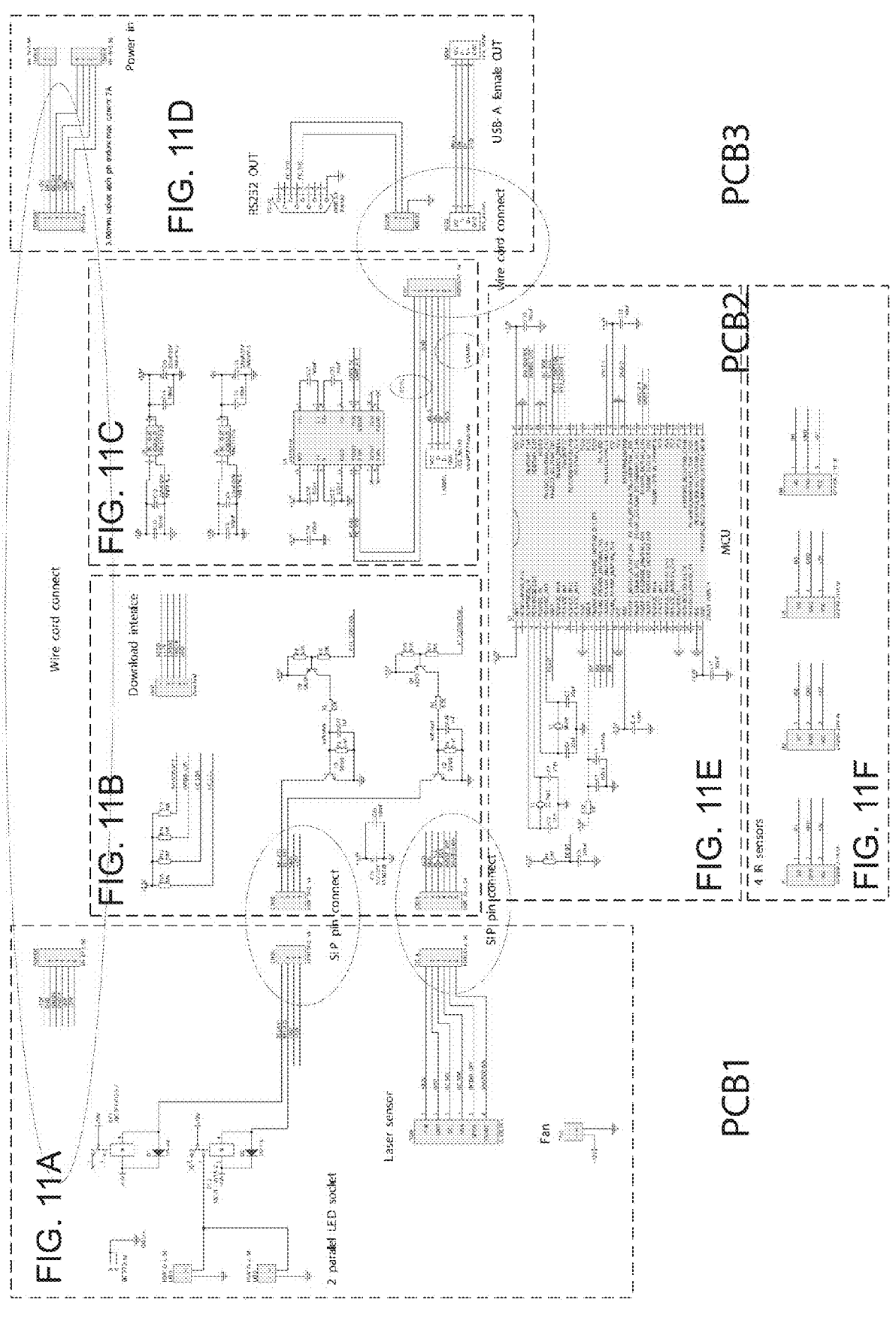

PCB2

Download Interface

PCB2

PCB2

4 IR sensors

PCB3

WIRE CORD CONNECT
FROM A →

POWERD

| 1 | +12V |
| 2 | GND |
| 3 | GND24 |
| 4 | GND24 |
| 5 | +12V |
| 6 | +12V |

VH-6Y-3.96

WIRE CORD CONNECT B 3.96mm socket each pin endure max current 7A

VH-2Y-3.96
+24VIN

| 1 |
| 2 |

| 4 |
| 3 |
| 2 |
| 1 |

+24VIN
VH-4Y-3.96

Power in

RS232 OUT
RS232

1
6
2   PC_RXD
7
3   PC_TXD
8
4
9
5

DB9RA/F
(FEMALE)

RS232B 3
2
1

HDR1X3 wire cord connect
from CN3

USB2

| VCC | 1 |
| D- | 2 |
| D+ | 3 |
| GND | 4 |

VBUS
DM
DP
GND

USB3

| 1 | VCC |
| 2 | D- |
| 3 | D+ |
| 4 | GND |

USB-A female OUT

USB_AF/90

FIG. 13A
Alpha HCoV-229E in normal human lung MRC5 fibroblasts
Green = Anti-human coronavirus spike glycoprotein; Blue= DAPI
FIG. 13B
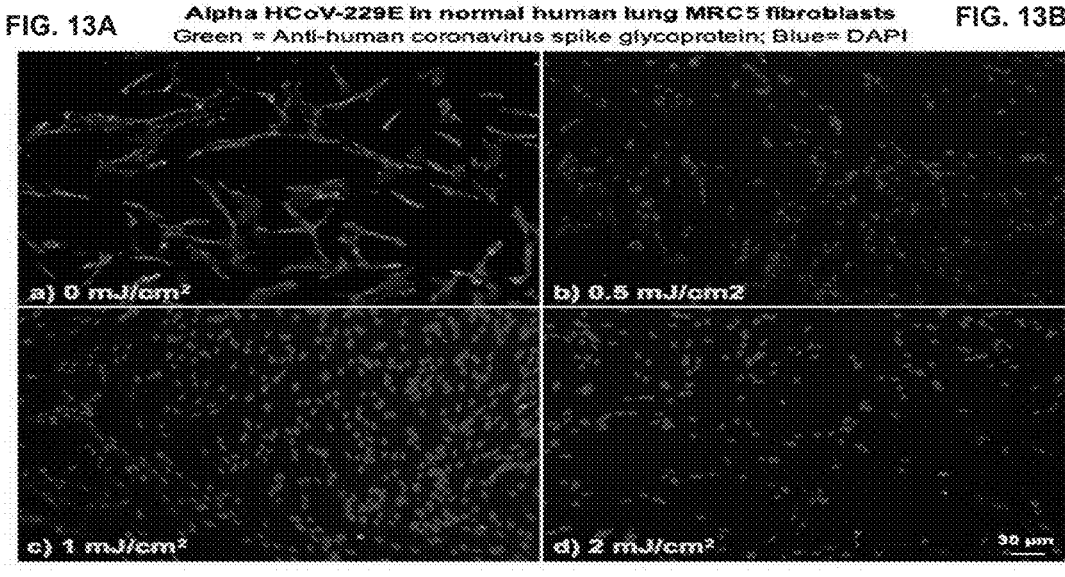
a) 0 mJ/cm²
b) 0.5 mJ/cm2
c) 1 mJ/cm²
d) 2 mJ/cm²
30 µm
FIG. 13C　　　　　　　　　　　FIG. 13D
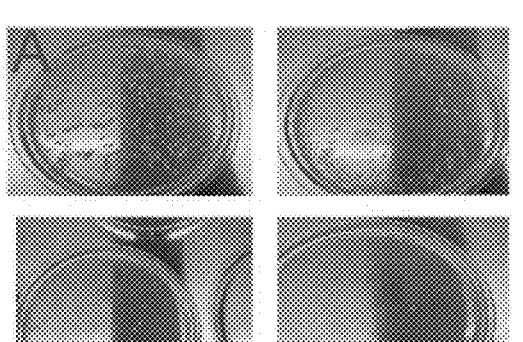
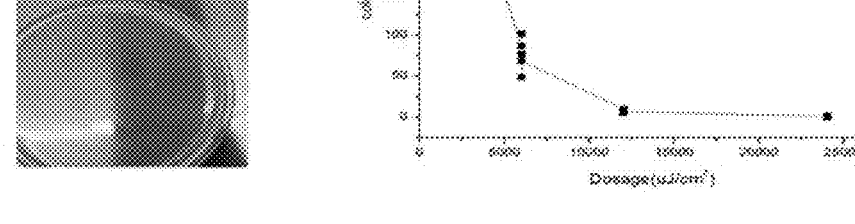
FIG. 14A　　　　　　　　　　　FIG. 14B

FIG. 19

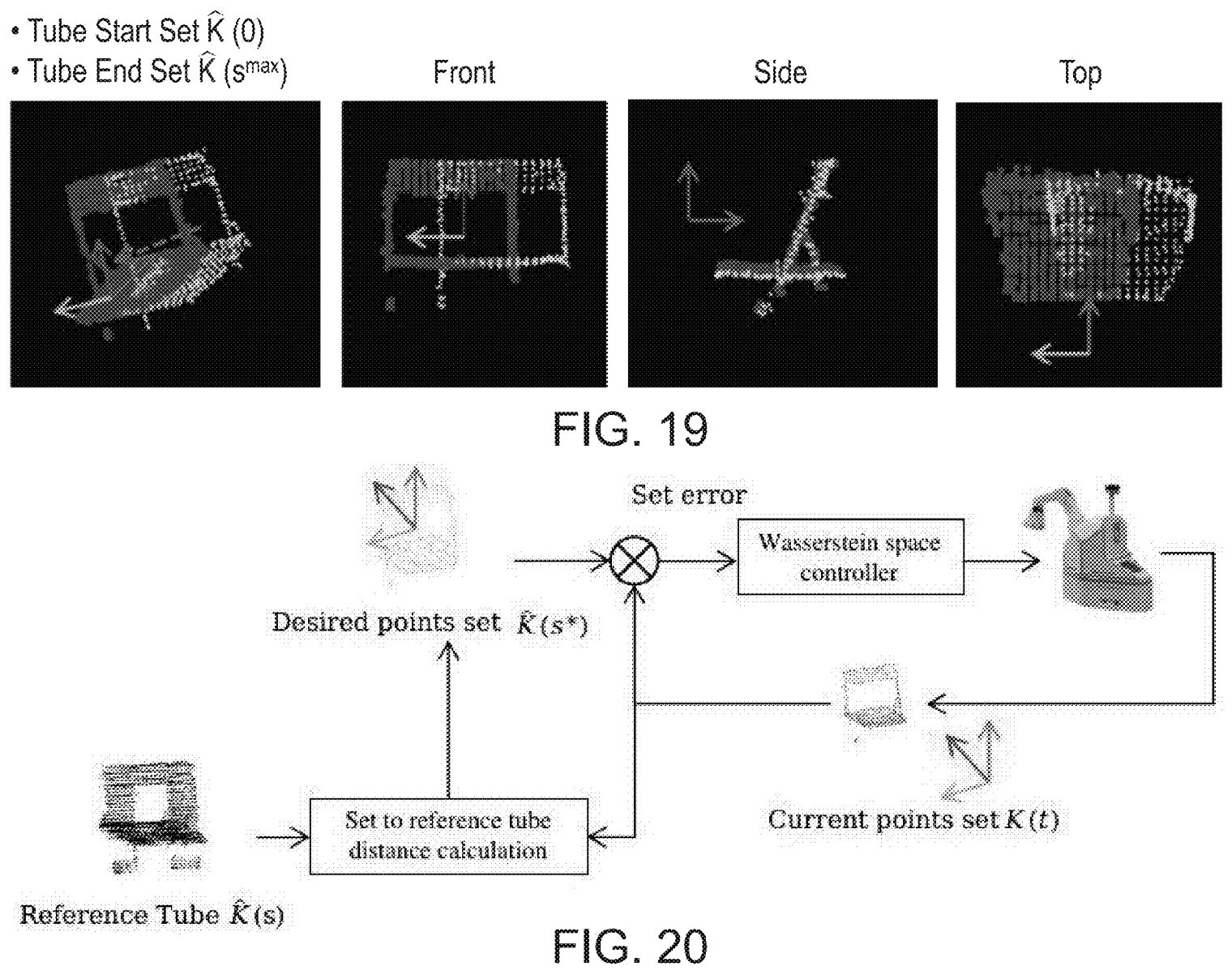

- Tube Start Set $\hat{K}(0)$
- Tube End Set $\hat{K}(s^{max})$

Front     Side     Top

FIG. 20

Set error

Wasserstein space controller

Current points set $K(t)$

Desired points set $\hat{K}(s^*)$

Set to reference tube distance calculation

Reference Tube $\hat{K}(s)$

DISINFECTION ROBOTS

CROSS-REFERENCE TO RELATED APPLICATION

The present application claims the benefit of priority to U.S. provisional patent application Ser. No. 63/270,246, filed Oct. 21, 2021, which is hereby incorporated by reference in its entirety.

FIELD OF THE INVENTION

The present invention relates to robots for cleaning areas and, more particularly, to robots for cleaning using ultraviolet light.

BACKGROUND OF THE INVENTION

Current surface sanitizing methods include spraying sanitizing chemicals or using UV light. There is no convincing evidence that spraying chemicals in the air is effective in sanitizing a space, since it is difficult to ensure that enough residual chemical settles down on the surfaces after spraying in the air. Furthermore, it is also difficult to directly spray a liquid form of chemical on surfaces due to the negative environmental impact and possible damage to the surfaces of items such as books.

Currently ultraviolet (UV) based disinfection lights are either fixed on walls or are placed on mobile bases. They are usually meters away from the surfaces that need the disinfection. The studies have shown that in order to achieve effective disinfection within a short period of time period the UV light has to be only a few centimeters away from the surface to be disinfected since UV with a wavelength in the range of 250 nano meters decays significantly while being transmitted through the air. Therefore, hours of irradiation time are usually required to achieve effective disinfection using presently available UV based disinfection systems. Currently there does not exist a product available in the market nor a prototype that can irradiate UV at a distance of a few centimeters away from surfaces to achieve disinfection within seconds.

The major difficulties are that the disinfection surfaces are large and have complicated shapes. Thus, it is not feasible to use current robot programming methods to generate a robot motion plan to control the motion of the robot so as to sweep over surfaces and irradiate them with UV from a few centimeters away.

SUMMARY OF THE INVENTION

According to the present invention a UV based surface disinfection system utilizes a UV light source that is mounted on a mobile robotic arm. The robot can be programmed to act autonomously. Thus, the robot can move to a selected place along the surface to be disinfected and the robot's arm is programmed to sweep over the surface at that place in order to bring the UV light source to within a distance of a few centimeters away from the surfaces, whereby effective and efficient surface disinfection is achieved Autonomous control is achieved with a framework that uses global localization as an initial condition. Then the control mainly compares a reference point cloud and a present point cloud in the end effector frame (E.E.F.) of the mobile manipulator based on Wasserstein distance. Then it outputs rigid special transformation information between them at low frequency (e.g., 10 Hz) and desired velocity information along the optimal path of the end effector at high frequency (e.g., 50 Hz).

BRIEF DESCRIPTION OF THE DRAWINGS

This patent or application file contains at least one drawing executed in color. Copies of this patent or patent application publication with color drawing(s) will be provided by the Office upon request and payment of the necessary fee.

The foregoing and other objects and advantages of the present invention will become more apparent when considered in connection with the following detailed description and appended drawings in which like designations denote like elements in the various views, and wherein:

FIGS. 13A to 13D show Alpha HCoV-229E in normal human lung MRC5 fibroblasts after exposure to continuous far UV-C in occupied public locations at the current regulatory exposure limit for 0 mJ/cm$^3$, 0.5 mJ/cm$^3$, 1 mJ/cm$^3$ and 2 mJ/cm$^3$, respectively;

FIG. 14A shows exposures of four cultures to UVC LED at 270 nm for 3000/0.5 min, 6000/1 min, 12000/2 min and 24000/3 min, and FIG. 14B shows a graph of the number of colonies versus dosage in uJ/cm2;

FIG. 19 shows a reference tube in a non-vector space as a 3-dimensional point set;

FIG. 20 is a block diagram of a single tube following a control framework in Wasserstein non-vector space;

DETAILED DESCRIPTION OF THE INVENTION

Figure 1:
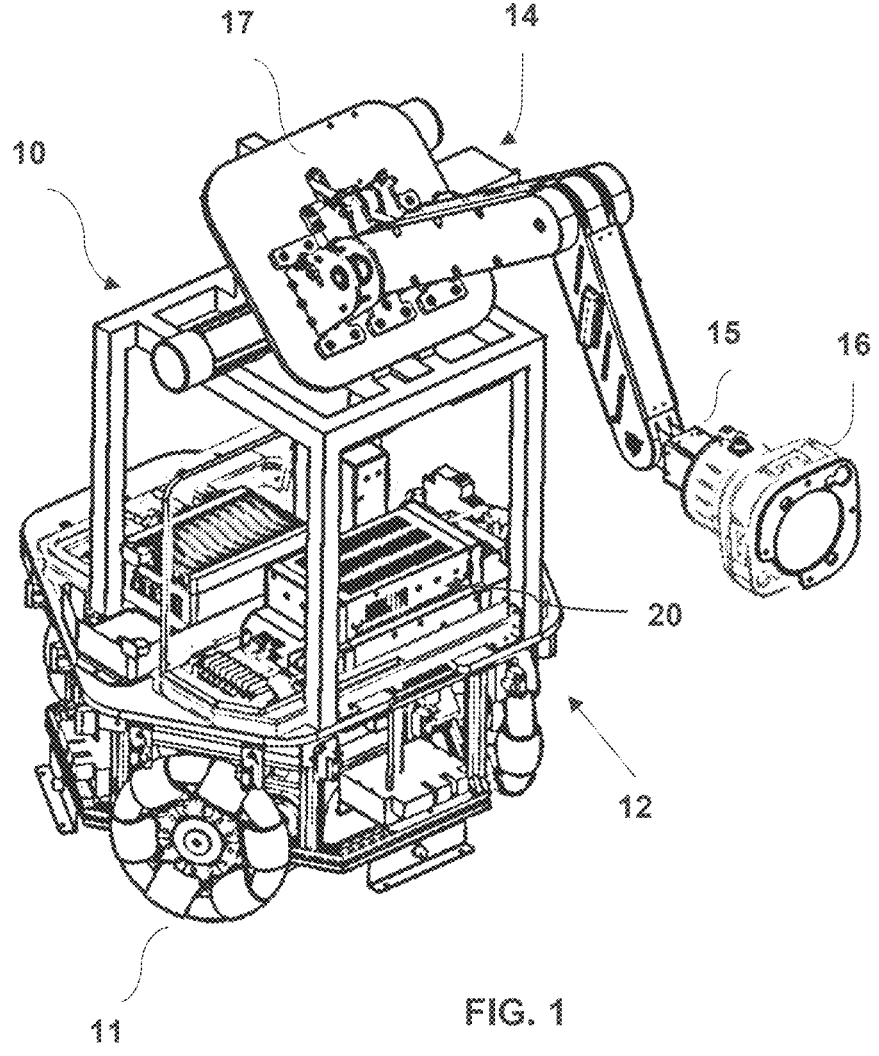
FIG. 1 is a perspective view of a disinfection robot with an Omni-wheel mobile base according to the present invention.

As shown in FIG. 1, the design of the disinfection robot 10 of the present invention has two main parts, a mobile base 12 and a universally positionable manipulator 14 with a UV lamp 16 at its end effector 15. The base 12 has three-Omni-directional wheels 11 that provide the advantage of being able to translation in any direction without turning. This will enable the robot to move in a narrow proximity.

The manipulator includes a LiDAR laser ranging module in the UVC lamp 16 at the end of the manipulator arm. It is used to measure the distance between the UVC lamp and the disinfected surface. In this way, the lamp is able to get much closer to the surface so as to improve the sterilization efficiency.

An electronic control system 20 for the robot is mounted on the base 12 and mainly consists of one processing board, e.g., a NVIDA Jetson which provides multiple neural networks in parallel for applications like image classification, object detection, segmentation, and speech processing. This processing board is used in the present invention for sensor information processing and task planning. The system also includes a microprocessor for robot control, e.g., a STMicroelectronics STM32. The on-board sensors include a multi-line laser scanner and a 360 degrees camera. The system communicates using Internet as well as cellular service. The architecture of the electronic system is illustrated in FIG. 2.

Figure 2:
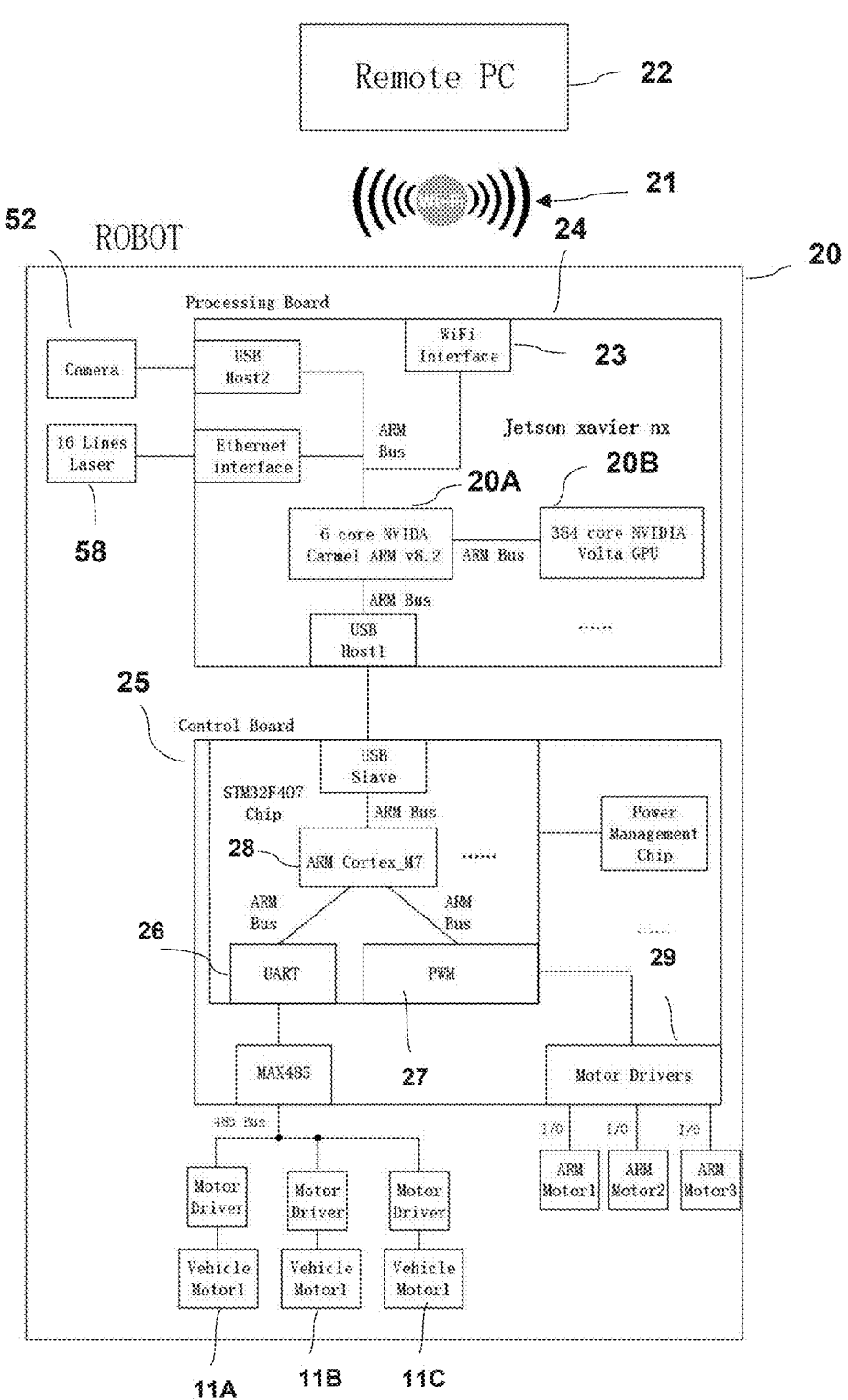
FIG. 2 is a block diagram of the electronic system of the disinfection robot of the present invention.

As shown in FIG. 2 a user can control the electronic system of the robot from a remote PC 22 over a WiFi or other transmission link. The remote signal is received by a WiFi interface or transceiver 23 located on a processing board 24. The signal is placed on an internal Advanced RISC Machine (ARM) bus. Further a USB camera 52 has its output directed to the ARM bus through a USB Host and a 16-line laser 58 has its output directed to the ARM bus through an Ethernet interface. The bus is connected to both a 6 core NVIDA Carmel ARM processor 20A and a 384 core NVIDIA Volta GPU 20B. The inputs are processed in these units to develop the planned trajectory and the output of the processing board 24 that holds these units is passed through a USB Host to a USB Slave on a Control Board 25.

An ARM Cortex processor 28 receives the processed signals and converts them into a drive signal for the wheels 11 and the movement of the joints on the manipulator 14. In particular the wheel drive signals pass to a universal asynchronous receiver-transmitter (UART) 26, which in turn divides the input into output signals for the motor drivers and motors for Omni wheels 11A, 11B and 11C on the robot base 12. The signals for the joints are passed through pulse with modulator circuit 27 and then to the motor drivers 29 and ARM motors for joints 1, 2 and 3.

Figure 3:
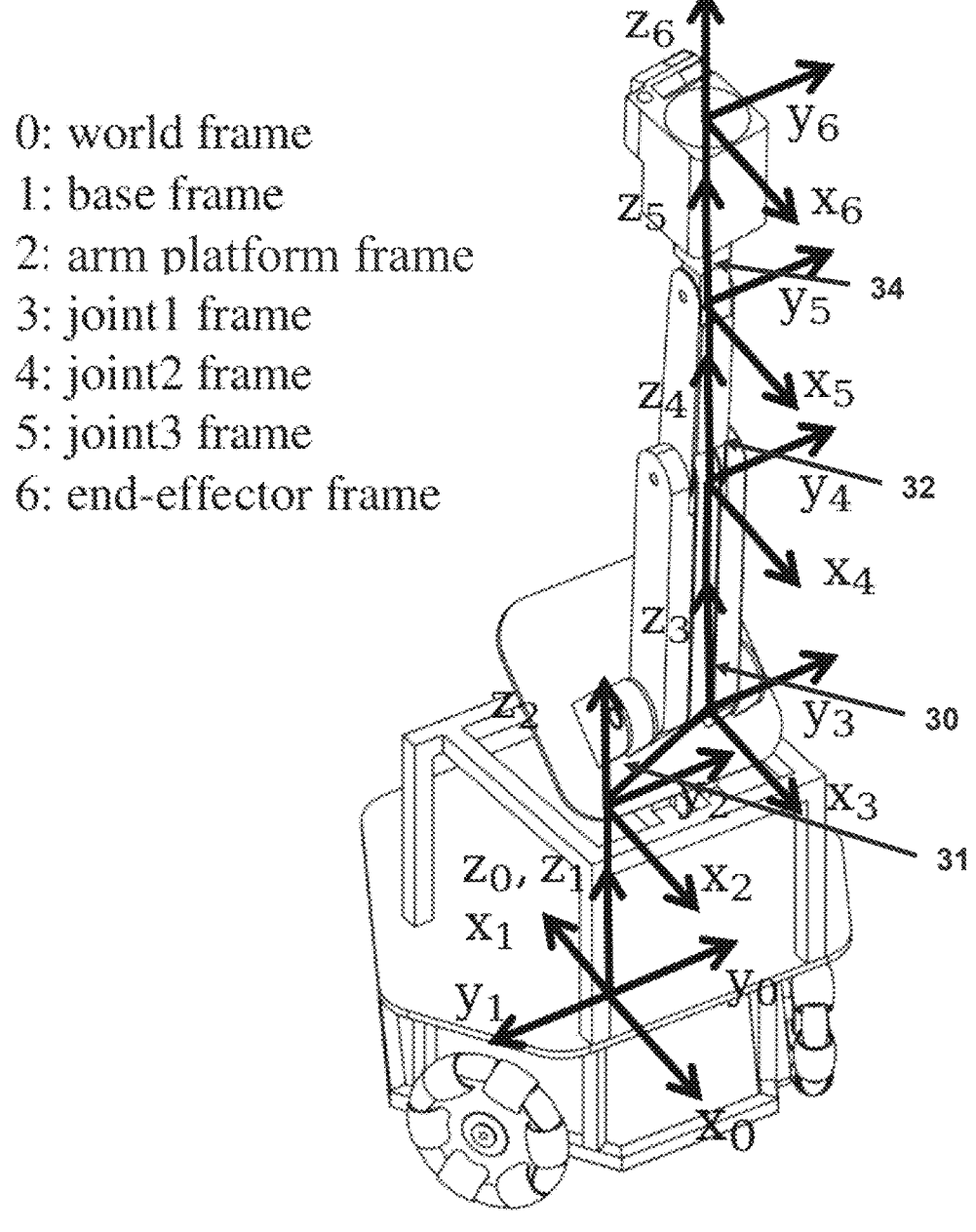
FIG. 3 is a diagram of the disinfection robot of the present invention showing a mobile manipulator and mobile robot coordinate systems.

As shown in FIG. 3, the universally positionable manipulator 14 of robot 10 has 3 rotation joints, which are located in three XYZ joint frames, i.e., no. 3 at 30, joint frame no. 4 at 32 and joint frame no. 5 at 34, respectively. The mobile base is located on frame no. 1 at 31. Each joint can have coordinates in xyz space as indicated, e.g., for joint 30 there are $x_3$, $y_3$ and $z_3$ axes. Further, mobile base 12 can move in the $x_1$, $y_1$ and $z_1$ axes. The equations for motion are as follows:

$$
{}^0_1T = \begin{bmatrix} -C_z & S_z & 0 & x_{01} \\ -S_z & -C_z & 0 & y_{01} \\ 0 & 0 & 1 & z_{01} \\ 0 & 0 & 0 & 1 \end{bmatrix}, {}^1_2T = \begin{bmatrix} 1 & 0 & 0 & x_{12} \\ 0 & 1 & 0 & y_{12} \\ 0 & 0 & 1 & z_{12} \\ 0 & 0 & 0 & 1 \end{bmatrix},
$$

$$
{}^2_3T = \begin{bmatrix} C_1 & 0 & S_1 & x_{23} \\ 0 & 1 & 0 & y_{23} \\ -S_1 & 0 & C_1 & z_{23} \\ 0 & 0 & 0 & 1 \end{bmatrix}, {}^3_4T = \begin{bmatrix} C_2 & 0 & S_2 & 0 \\ 0 & 1 & 0 & 0 \\ -S_2 & 0 & C_2 & L_1 \\ 0 & 0 & 0 & 1 \end{bmatrix},
$$

$$
{}^4_5T = \begin{bmatrix} C_3 & 0 & S_3 & 0 \\ 0 & 1 & 0 & 0 \\ -S_3 & 0 & C_3 & L_2 \\ 0 & 0 & 0 & 1 \end{bmatrix}, {}^5_6T = \begin{bmatrix} 1 & 0 & 0 & 0 \\ 0 & 1 & 0 & 0 \\ 0 & 0 & 1 & L_3 \\ 0 & 0 & 0 & 1 \end{bmatrix}
$$

$$
{}^0_6T = {}^0_1T {}^1_2T {}^2_3T {}^3_4T {}^4_5T {}^5_6T = \begin{bmatrix} -C_zC_{123} & S_z & -S_{123}C_z & A \\ -S_zC_{123} & -C_z & -S_{123}S_z & B \\ -S_{123} & 0 & C_{123} & C \\ 0 & 0 & 0 & 1 \end{bmatrix},
$$

$A = x_{01} + S_z(y_{12} + y_{23}) - C_z(x_{12} + x_{23}) - C_z(L_3S_{123} + L_2S_{12} + L_1S_1)$, $B = y_{01} - C_z(y_{12} + y_{23}) - S_z(x_{12} + x_{23}) - S_z(L_3S_{123} + L_2S_{12} + L_1S_1)$, $C = z_{01} + z_{12} + z_{23} + L_3C_{123} + L_2C_{12} + L_1C_1$ where $S_z$ and $C_z$ equal $\sin(\theta_z)$ and $\cos(\theta_z)$, respectively; Oz means current orientation of the mobile platform; $S_1$ and $C_1$ equal $\sin(q_1)$ and $\cos(q_1)$, respectively; $q_1$ is the angle value of the joint 1; $S_{12}$ and $C_{12}$ equal $\sin(q_1+q_2)$ and $\cos(q_1+q_2)$, respectively; $q_2$ is the angle value of the joint 2; $S_{123}$ and $C_{123}$ equal $\sin(q_1+q_2+q_3)$ and $\cos(q_1+q_2+q_3)$, respectively; $q_3$ is the angle value of the joint 3; $L_1$, $L_2$ and $L_3$ are the length of link on the robot arm.

The inverse kinematics are determined as follows:

$$q_2 =$$

$$\mathrm{Atan2}\left( \pm \sqrt{1 - \left( \frac{x_{ee}^2 + y_{ee}^2 + z_{ee}^2 - L_1^2 - L_2^2}{2L_1L_2} \right)^2}, \left( \frac{x_{ee}^2 + y_{ee}^2 + z_{ee}^2 - L_1^2 - L_2^2}{2L_1L_2} \right) \right)$$

$$q_1 = \mathrm{Atan2}\left( z_{ee}, \sqrt[2]{x_{ee}^2 + y_{ee}^2} \right) \mathrm{Atan2}\left( \pm L_2 \sqrt{1 - \left( \frac{x_{ee}^2 + y_{ee}^2 + z_{ee}^2 - L_1^2 - L_2^2}{2L_1L_2} \right)^2}, \right.$$

$$\left. \left( L_1 + L_2 \left( \frac{x_{ee}^2 + y_{ee}^2 + z_{ee}^2 - L_1^2 - L_2^2}{2L_1L_2} \right) \right) \right)$$

$$q_3 = \mathrm{Atan2}(n_y, n_x) - q_1 - q_2$$

$$P_x = x_0 - {}^2_0Tx_{ee}$$

$$P_y = y_0 - {}^2_0Ty_{ee}$$

$$\theta_z = \mathrm{Atan2}(y_{ee}, x_{ee})$$

-continued $$\theta_{front} = \frac{-P_y - L\theta_z}{R}$$

$$\theta_{left} = \frac{P_x \cos\left(\frac{\pi}{6}\right) + P_y \sin\left(\frac{\pi}{6}\right) - L\theta_z}{R}$$

$$\theta_{right} = \frac{-P_x \cos\left(\frac{\pi}{6}\right) + P_y \sin\left(\frac{\pi}{6}\right) - L\theta_z}{R}$$

where $x_{ee}$ is the distance from end end-effector 15 to the arm platform frame along the X axis of arm platform frame; $y_{ee}$ is the distance from the end-effector to the arm platform along the Y axis of arm platform frame; $z_{ee}$ is the distance from the end-effector to arm platform along the Z axis of arm platform frame; $n_x$ and $n_y$ belong to the rotation matrix; $x_0$, $y_0$ are the position of the end-effector on the world reference frame (W.R.F.); $P_x$, $P_y$ and $\theta_z$ are the pose of the mobile platform; $\theta_{front}$, $\theta_{left}$ and $\theta_{right}$ are the angle of wheel 11 of the mobile platform 12; L is the distance between center of the mobile platform and the wheel 11; R is the radius of wheel 11; and $_0^2T$ is a transformation matrix from no. 2 frame to no. 0 frame.

The Jacobian matrix is defined as:

$$_0^6\binom{v}{w} = [J_{arm} \quad J_{base}]\begin{bmatrix}\dot{\theta}_a \\ \dot{\theta}_a\end{bmatrix}$$

$$J_{arm} = \begin{bmatrix} C_z(L_3 C_{123} + L_2 C_{12} + L_1 C_1) & C_z(L_3 C_{123} + L_2 C_{12}) & C_z L_3 C_{123} \\ -S_z(L_3 C_{123} + L_2 C_{12} + L_1 C_1) & -S_z(L_3 C_{123} + L_2 C_{12}) & -S_z L_3 C_{123} \\ -L_3 S_{123} - L_2 S_{12} - L_1 S_1 & -L_3 S_{123} - L_2 S_{12} & -L_3 S_{123} \\ S_z & S_z & S_z \\ -C_z & -C_z & -C_z \\ 0 & 0 & 0 \end{bmatrix},$$

$$J_{base} = \begin{bmatrix} -\frac{2}{3}R\cos\frac{\pi}{6} & 0 & \frac{2}{3}R\cos\frac{\pi}{6} \\ \frac{R}{3} & -\frac{2R}{3} & \frac{R}{3} \\ 0 & 0 & 0 \\ 0 & 0 & 0 \\ 0 & 0 & 0 \\ -\frac{R}{3L} & -\frac{R}{3L} & -\frac{R}{3L} \end{bmatrix}$$

where $\dot{\theta}_a$ is a vector of joint velocity and $\dot{\theta}_b$ is a vector of wheel velocity.

Dynamics modeling is achieved by the following equations:

$$D(q)\ddot{q} + C(q, \dot{q})\dot{q} + g(q) = \tau$$

$$D(q) = \left[\sum_{k=1}^n \left\{m_i J_{v_i}(q)^T J_{v_i}(q) + J_{\omega_i}(q)^T R_i(q) I_i R_i(q)^T J_{\omega_i}(q)\right\}\right],$$

$$C(q, \dot{q}) = \sum_{k=1}^n c_{ijk}(q)\dot{q} = \sum_{k=1}^n \frac{1}{2}\left\{\frac{\partial d_{kj}}{\partial q_i} + \frac{\partial d_{kj}}{\partial q_j} - \frac{\partial d_{ij}}{\partial q_k}\right\}\dot{q},$$

$$g(q) = [g_1(q), g_2(q), g_3(q), g_4(q)]^T,$$

$$J_{v_{c1}}(q) = \begin{bmatrix} -C_z L_{c1} C_1 & 0 & 0 & -\frac{2}{3}R\cos\frac{\pi}{6} & 0 & \frac{2}{3}R\cos\frac{\pi}{6} \\ S_z L_{c1} C_1 & 0 & 0 & \frac{R}{3} & -\frac{2R}{3} & \frac{R}{3} \\ -L_{c1}S_1 & 0 & 0 & 0 & 0 & 0 \end{bmatrix},$$

$$J_{v_{c2}}(q) = \begin{bmatrix} -C_z(L_{c2}C_{12} + L_1 C_1) & -C_z L_{c2} C_{12} & 0 & -\frac{2}{3}R\cos\frac{\pi}{6} & 0 & \frac{2}{3}R\cos\frac{\pi}{6} \\ S_z(L_{c2}C_{12} + L_1 C_1) & S_z L_{c2} C_{12} & 0 & \frac{R}{3} & -\frac{2R}{3} & \frac{R}{3} \\ -L_{c2}S_{12} - L_1 S_1 & -L_{c2}S_{12} & 0 & 0 & 0 & 0 \end{bmatrix},$$

$$J_{v_{c3}}(q) = \begin{bmatrix} -C_z(L_{c3}C_{123} + L_2 C_{12} + L_1 C_1) & -C_z(L_{c3}C_{123} + L_2 C_{12}) & -C_z L_{c3} C_{123} & -\frac{2}{3}R\cos\frac{\pi}{6} & 0 & \frac{2}{3}R\cos\frac{\pi}{6} \\ S_z(L_{c3}C_{123} + L_2 C_{12} + L_1 C_1) & S_z(L_{c3}C_{123} + L_2 C_{12}) & S_z L_{c3} C_{123} & \frac{R}{3} & -\frac{2R}{3} & \frac{R}{3} \\ -L_{c3}S_{123} - L_2 S_{12} - L_1 S_1 & -L_{c3}S_{123} - L_2 S_{12} & -L_{c3}S_{123} & 0 & 0 & 0 \end{bmatrix},$$

$$J_{v_{c4}}(q) = \begin{bmatrix} 0 & 0 & 0 & -\frac{2}{3}R\cos\frac{\pi}{6} & 0 & \frac{2}{3}R\cos\frac{\pi}{6} \\ 0 & 0 & 0 & 0 & 0 & 0 \\ 0 & 0 & 0 & 0 & 0 & 0 \end{bmatrix}$$

$$J_{v_{c5}}(q) = \begin{bmatrix} 0 & 0 & 0 & 0 & 0 & 0 \\ 0 & 0 & 0 & \frac{R}{3} & -\frac{2R}{3} & \frac{R}{3} \\ 0 & 0 & 0 & 0 & 0 & 0 \end{bmatrix}$$

$$J_{\omega_1}(q) = \begin{bmatrix} S_z & 0 & 0 & 0 & 0 & 0 \\ -C_z & 0 & 0 & 0 & 0 & 0 \\ 0 & 0 & 0 & -\frac{R}{3L} & -\frac{R}{3L} & -\frac{R}{3L} \end{bmatrix},$$

$$J_{\omega_2}(q) = \begin{bmatrix} S_z & S_z & 0 & 0 & 0 & 0 \\ -C_z & -C_z & 0 & 0 & 0 & 0 \\ 0 & 0 & 0 & -\frac{R}{3L} & -\frac{R}{3L} & -\frac{R}{3L} \end{bmatrix},$$

$$J_{\omega_3}(q) = \begin{bmatrix} S_z & S_z & S_z & 0 & 0 & 0 \\ -C_z & -C_z & -C_z & 0 & 0 & 0 \\ 0 & 0 & 0 & -\dfrac{R}{3L} & -\dfrac{R}{3L} & -\dfrac{R}{3L} \end{bmatrix},$$

$$J_{\omega_6}(q) = \begin{bmatrix} 0 & 0 & 0 & 0 & 0 & 0 \\ 0 & 0 & 0 & 0 & 0 & 0 \\ 0 & 0 & 0 & -\dfrac{R}{3L} & -\dfrac{R}{3L} & -\dfrac{R}{3L} \end{bmatrix},$$

$$P = m_1 g L_{c1} S_1 + m_2 g (L_1 S_1 + L_{c2} S_{12}) + m_3 g (L_1 S_1 + L_2 S_{12} + L_{c3} S_{123}) + m_4 g,$$

$$g_i(q) = \frac{\partial P}{\partial q_i}$$

where $D(q)$ is the inertia matrix; $C(q,\dot{q})$ is the Coriolis matrix; $g(q)$ is the gravitational potential energy; $J_{v_i}(q)$ is the linear velocity Jacobian matrix of i-th joint; $J_{\omega_i}(q)$ is the angular velocity of the Jacobian matrix of i-th joint; $RI(q)$ is rotation matrix; $II$ is the inertia tensor; $d_{ij}$ is an element in the inertia matrix; $L_{ci}$ is the distance between i-th joint and the center of i-th link; $m_1$, $m_2$ and $m_3$ are the weight of Link 1, Link 2 and Link 3, respectively; and $m_4$ is the weight of mobile platform.

During Motion planning, the velocity, acceleration, position and time according to the known initial and end points are acquired. Based on this information a plan is generated to control the end-effector so it follows a desired trajectory. When planning this trajectory, it is divided into three sections: third-order, fifth-order and third-order trajectory, as shown in the following formula.

$$t_0 \rightarrow t_1 : a_{13} t^3 + a_{12} t^2 + a_{11} t + a_{10} = x(t)$$

$$t_1 \rightarrow t_2 a_{25} t^5 + a_{24} t^4 + a_{23} t^3 + a_{22} t^2 + a_{21} t + a_{20} = x(t)$$

$$t_2 \rightarrow t_f : a_{33} t^3 + a_{32} t^2 + a_{31} t + a_{30} = x(t)$$

After performing the 3-5-3 order trajectories in the planner, the pose of each point in task space can be transformed into joint space to control the robot's joint through inverse kinematics and a Jacobian matrix as shown above. The pose of a robot provides information on the location of the robot in either two or three dimensions and also its orientation. For mobile robots, the pose can be a simple three element vector, but for arm-based robots, a matrix is often used to describe the pose. Therefore, in joint space, the joint controller can publish commands to control the joint based on the position and velocity, where the velocity and position correspond to a specific time.

In the controller system, the input contains two parts: feedforward and feedback. The first part (feedforward) is acquired through the Dynamics model indicated above to compute the torque in the controller, and the formula of torque is set forth below. The second part (feedback) is the position and velocity. Based on the position and velocity error, the position loop and velocity loop are constructed. Then the feedforward of torque is combined with the position loop and velocity loop to calculate the decoupling output. The controller output is torque. This torque value satisfies the requirement of the entire robot system in order to realize a target, including mutual influence between each joint. Finally, the torque output is provided to the driver for the manipulator, and the driver generates current to make the manipulator motors operate according to the corresponding torque. The formulas for torque are $$\tau_1 =$$

$$d_{11}\ddot{q}_1 + d_{12}\ddot{q}_2 + d_{13}\ddot{q}_3 + d_{14}\ddot{q}_4 + d_{15}\ddot{q}_5 + d_{16}\ddot{q}_6 + \sum_{i=1}^{6}\sum_{j=1}^{6} c_{ij1}(q)\dot{q}_i\dot{q}_j + g_1(q)$$

$$\tau_2 =$$

$$d_{21}\ddot{q}_1 + d_{22}\ddot{q}_2 + d_{23}\ddot{q}_3 + d_{24}\ddot{q}_4 + d_{25}\ddot{q}_5 + d_{26}\ddot{q}_6 + \sum_{i=1}^{6}\sum_{j=1}^{6} c_{ij2}(q)\dot{q}_i\dot{q}_j + g_2(q)$$

$$\tau_3 =$$

$$d_{31}\ddot{q}_1 + d_{32}\ddot{q}_2 + d_{33}\ddot{q}_3 + d_{34}\ddot{q}_4 + d_{35}\ddot{q}_5 + d_{36}\ddot{q}_6 + \sum_{i=1}^{6}\sum_{j=1}^{6} c_{ij3}(q)\dot{q}_i\dot{q}_j + g_3(q)$$

$$F_x =$$

$$d_{41}\ddot{q}_1 + d_{42}\ddot{q}_2 + d_{43}\ddot{q}_3 + d_{44}\ddot{q}_4 + d_{45}\ddot{q}_5 + d_{46}\ddot{q}_6 + \sum_{i=1}^{6}\sum_{j=1}^{6} c_{ij4}(q)\dot{q}_i\dot{q}_j + g_4(q)$$

$$F_y =$$

$$d_{51}\ddot{q}_1 + d_{52}\ddot{q}_2 + d_{53}\ddot{q}_3 + d_{54}\ddot{q}_4 + d_{55}\ddot{q}_5 + d_{56}\ddot{q}_6 + \sum_{i=1}^{6}\sum_{j=1}^{6} c_{ij5}(q)\dot{q}_i\dot{q}_j + g_5(q)$$

$$M_z =$$

$$d_{61}\ddot{q}_1 + d_{62}\ddot{q}_2 + d_{63}\ddot{q}_3 + d_{64}\ddot{q}_4 + d_{65}\ddot{q}_5 + d_{66}\ddot{q}_6 + \sum_{i=1}^{6}\sum_{j=1}^{6} c_{ij6}(q)\dot{q}_i\dot{q}_j + g_6(q)$$

$$\begin{bmatrix} \tau_{right} \\ \tau_{front} \\ \tau_{left} \end{bmatrix} = \begin{bmatrix} -\dfrac{2}{3}R\cos\dfrac{\pi}{6} & \dfrac{R}{3} & -\dfrac{R}{3L} \\ 0 & -\dfrac{2R}{3} & -\dfrac{R}{3L} \\ \dfrac{2}{3}R\cos\dfrac{\pi}{6} & \dfrac{R}{3} & -\dfrac{R}{3L} \end{bmatrix} \begin{bmatrix} F_x \\ F_y \\ M_z \end{bmatrix}$$

Where $\tau_1$, $\tau_2$ and $\tau_3$ are the torque of joint 1, joint 2 and joint 3 respectively; $\tau_{right}$, $\tau_{front}$ and $\tau_{left}$ are the torque of the wheel in the mobile platform; $d_{ij}$ is the element in the inertia matrix; $c_{ijk}$ is the Coriolis matrix of k-th joint; $g(q)$ is the gravitational potential energy; and $F_x$, $F_y$ and $M_z$ are the driving force and moment applied to the mobile platform.

Figure 4:
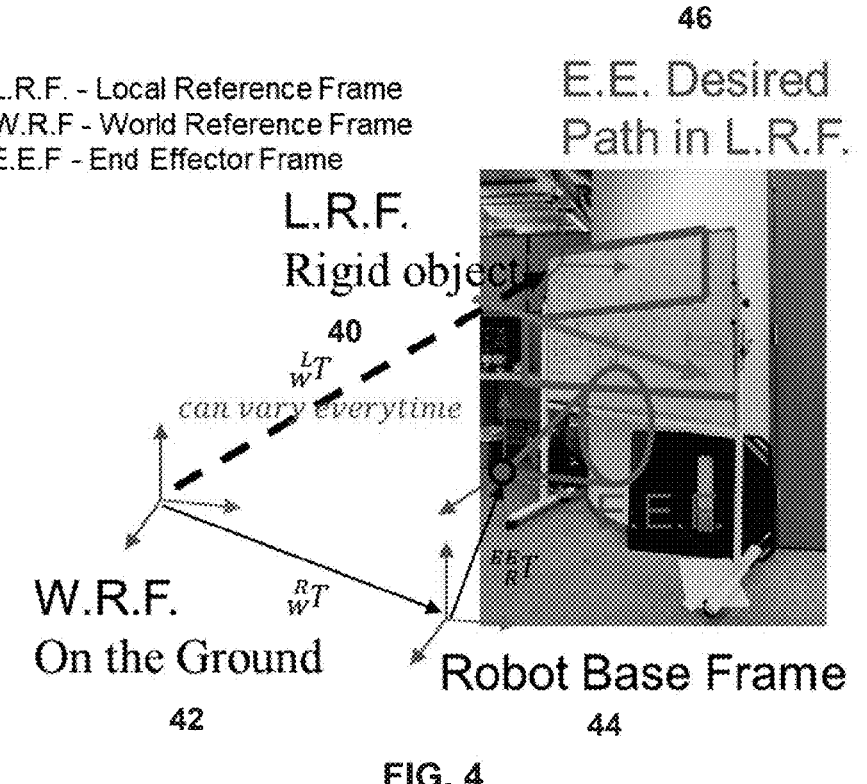
FIG. 4 shows an uncertain pose of an object in a world reference frame (W.R.F)

It is vital for the robot to have robustness and flexibility when executing mobile manipulation tasks, such as indoors disinfection. However, there are difficulties in mobile manipulation tasks in unstructured environments. To be more specific, there are three main challenges in indoor mobile manipulation As shown in FIG. 4, the object to be disinfected, e.g., the white board, can be movable, then $_W^L T$ can vary from time to time. Then it is almost impossible to finish the task with a path described in the world reference frame (W.R.F.). In FIG. 4 the rigid object 40 is a movable white board. It can be located in W.R.F coordinates 42. The robot base frame also has a set of coordinates 44 and the end effector frame (E.E.F.) has a limited range (red circle) which only partially engages the white board and could not by itself plot the desired path 46, which zig zags across the surface of the white board as shown.

Figure 5A:
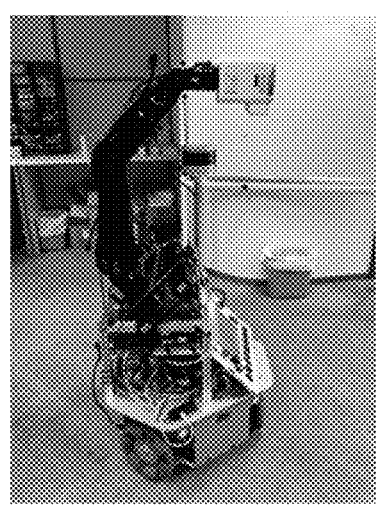
FIGS. 5A and 5B show images of the mobile manipulator of the present invention in different unstructured environments.
Figure 5B:

FIG. 5 illustrates two an unstructured environments, like an office, library and so on, that may have unstable and inaccurate localization based on a global point cloud map due to occlusion (blocking) of the LiDAR's path to the desired object, changes of environment (movement of objects), etc. Also, the robot can be interrupted in lots of ways (e.g., a person standing in the way of the movable base or manipulator), so the robot is expected to respond smartly and safely to those interruptions. Then the robot should recover and go on to complete the unfinished task smoothly and quickly.

Figure 6:
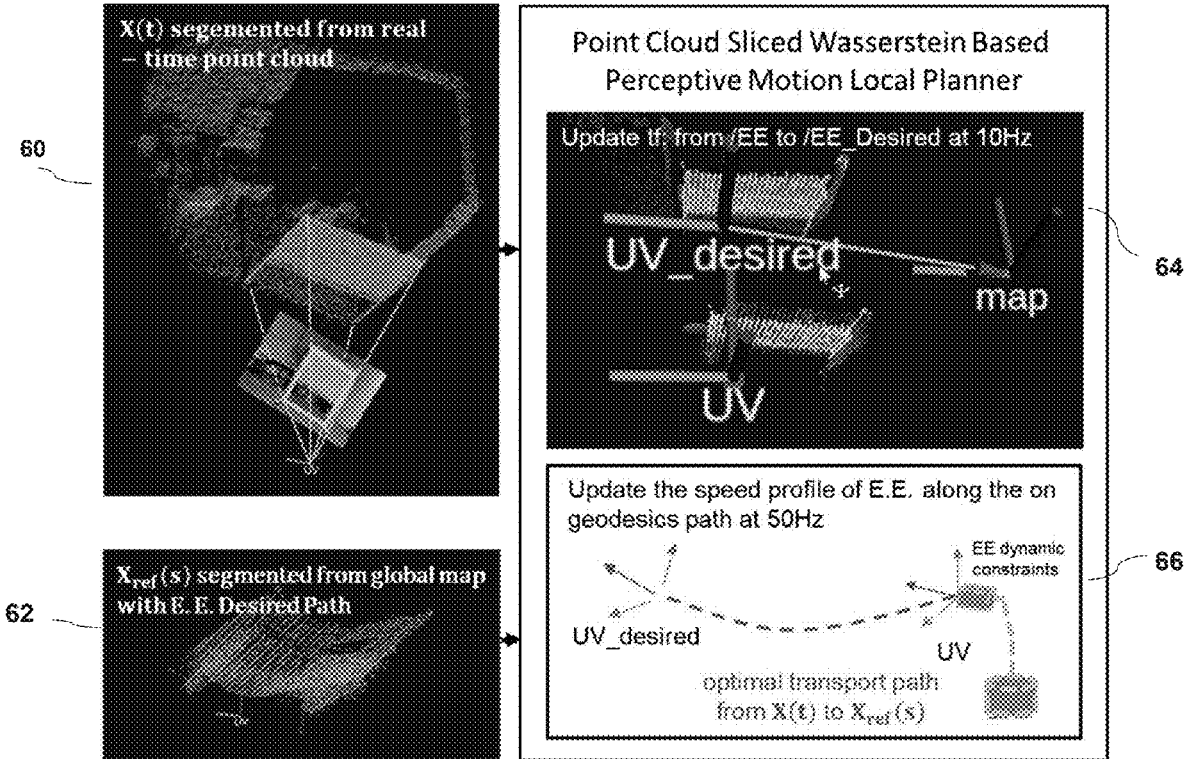
FIG. 6 is a schematic diagram of an "Object Perceptive Local Planer" with point cloud acquisition and point cloud registration-based vector space/sliced Wasserstein distance based non-vector space controllers in the end effector (UV light) frame according to the present invention.

The "Object Perceptive Local Planer" method of the present invention as shown in FIG. 6 is designed to realize this objective. As shown in FIG. 6 at 60, X(t) segments are segmented from a real-time point cloud. At 62 $X_{ref}(s)$ segments are segmented from a global map as the end effector's desired path. A point cloud sliced Wasserstein based perceptive motion local planner 64 uses the selected segments X(t) from step 60 to map the UV desired path compared to the actual UV path. The comparison is updated at a rate of 10 Hz. At step 64 the speed profile of the end effector is updated along the geodesics path at 50 Hz. Thus, the optimal transport path from X(t) to $X_{ref}(s)$ is established.

Figure 7:
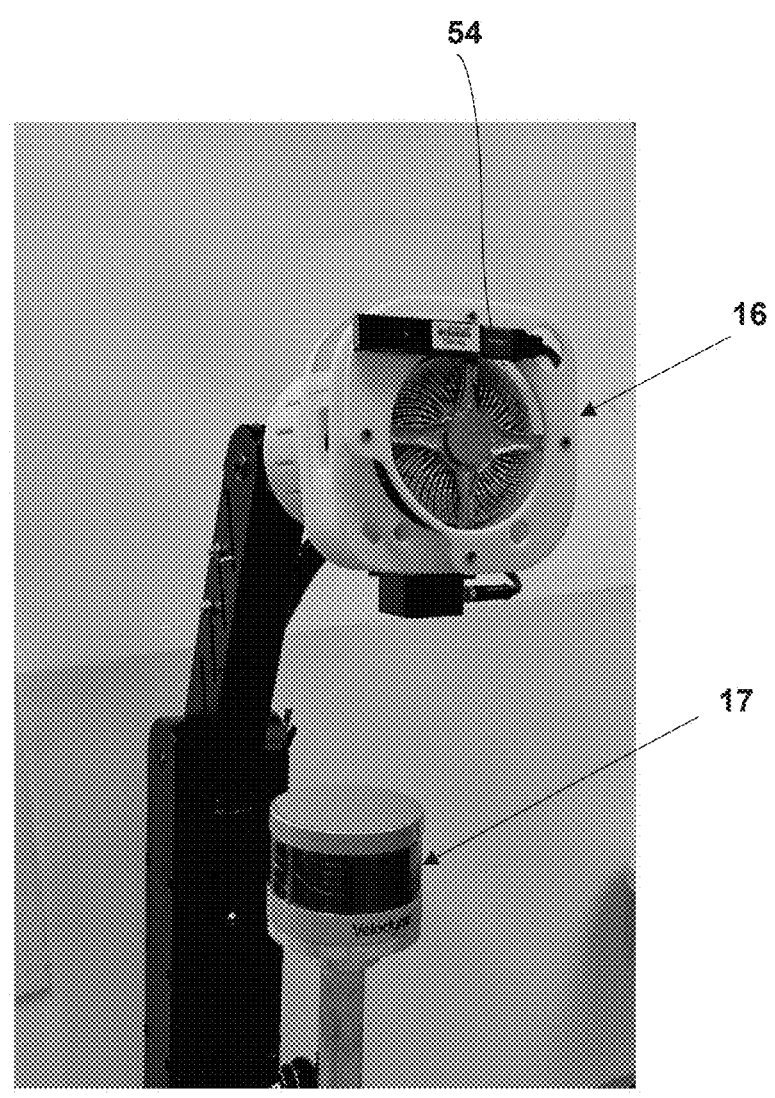
FIG. 7 is an image of a Light Detection and Ranging (LiDAR) module on an arm of the robot of the present invention and a time of flight (ToF) camera at the end effector (E.E) of the mobile manipulator.

One key to this process is that the motion planning and controlling steps utilize both spatial and shape information about an object of interest in the global frame to adapt to unexpected disturbances in the robot local frame. The "Object Perceptive Local Planer" takes advantage of a time-of-flight (ToF) camera 54 attached to the UV light 16 at the end-effector (E.E.) and the Light Detection and Ranging (LiDAR) device 17 on the robot base as shown in FIG. 7. A ToF camera is a range imaging camera system employing time-of-flight techniques to resolve the distance between the camera and the subject for each point of an image, by measuring the round-trip time of an artificial light signal provided by a laser. Laser-based time-of-flight cameras are part of a broader class of scannerless LIDAR, in which the entire scene is captured with each laser pulse, as opposed to point-by-point with a laser beam such as in scanning LIDAR systems.

Figure 8:
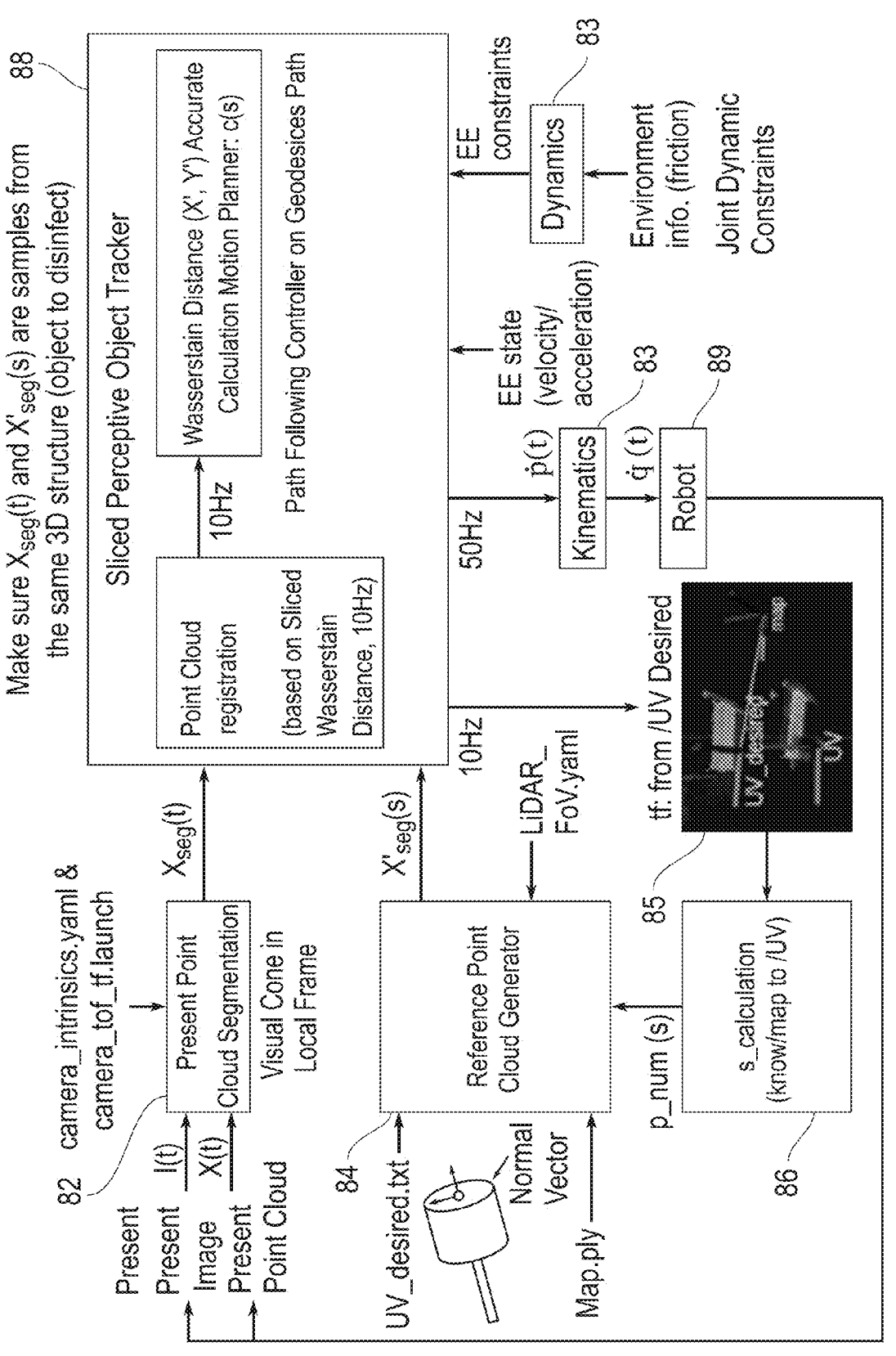
FIG. 8 shows the detailed framework of "Object Perceptive Local Planer" during a complete disinfection process on a movable object.

The overall framework of the Algorithm is shown in FIG. 8. As can be seen in FIG. 8, a present point cloud segmentation 82 receives a present image I(t) and a present point cloud X(t) from the robot. Also input to the circuit of FIG. 8 are the signals camera_intrinsics.yami & camera_tof_If.launch, whose use is described below. Unit 82 provides a visual cone in the local frame and produces $X_{seg}(t)$ that is delivered to Object Perceptive Tracker (point cloud registration-based vector space/sliced Wasserstein distance based non-vector space controllers) unit 88. Reference point cloud generator 84 receives UV_desired.txt, Map.ply and p_num (s) from which it generates $X'_{seg}(s)$, which is applied to unit 88. Unit 88 also receives E.E. State (velocity acceleration) and E.E. constraints. The E.E. constraints come from joint dynamic constraints and environmental information (e.g., friction) after passing through dynamics module 87.

The sliced perceptive object tracker 88 engages in trajectory planning with dynamic constraints on the geodesics path and Wasserstein barycentre as intersections from X to X'. Tracker 88 produces as an output to the point cloud registration (based on sliced Wasserstein distance) at a rate of 10 Hz, which is passed to the point cloud sliced Wasserstein based perceptive motion local planner 85 (which is equivalent to unit 64 of FIG. 6). Planner 85 has its output tf: from/UV to/UV desired directed to generator 84 as an input along with $X'_{seg}(s)$ and LiDAR_FoV.yaml. A second output of the Planner 85 is applied to a calculation block 86 which engages in e_calculation (known/map to/UV). This block 86 provides the input P_num(s) to generator 84. Finally, an output p(T) at 50 Hz from tracker 88 is applied to kinematics unit 83 to create q(t) which is directed to the robot 89, which in turn provides the present image and present point cloud applied to unit 82.

In brief the framework uses global localization as an initial condition, then it mainly compares reference point cloud and present point cloud in the end effector frame (E.E.F.) of the mobile manipulator based on Wasserstein distance. Then it outputs rigid transformation information between them at low frequency and desired velocity information along the optimal path of the end effector at high frequency.

In E.E.F., Wasserstein Distance (X(t), X_ref (s)) leads to a rigid transform and an optimal transport plan with a geodesics path between them. Directly estimating the rigid transform of two-point clouds is time consuming. However, with the Wasserstein barycenter, as the intersections of two-point clouds, the transform can be rapidly obtained and is guaranteed to be on the shortest path in terms of optimal transport from the source point cloud to the destination. The main contribution of this part is to integrate the perception and control module together to provide "spatial perceptive ability" of the motion in real time.

Figure 9:
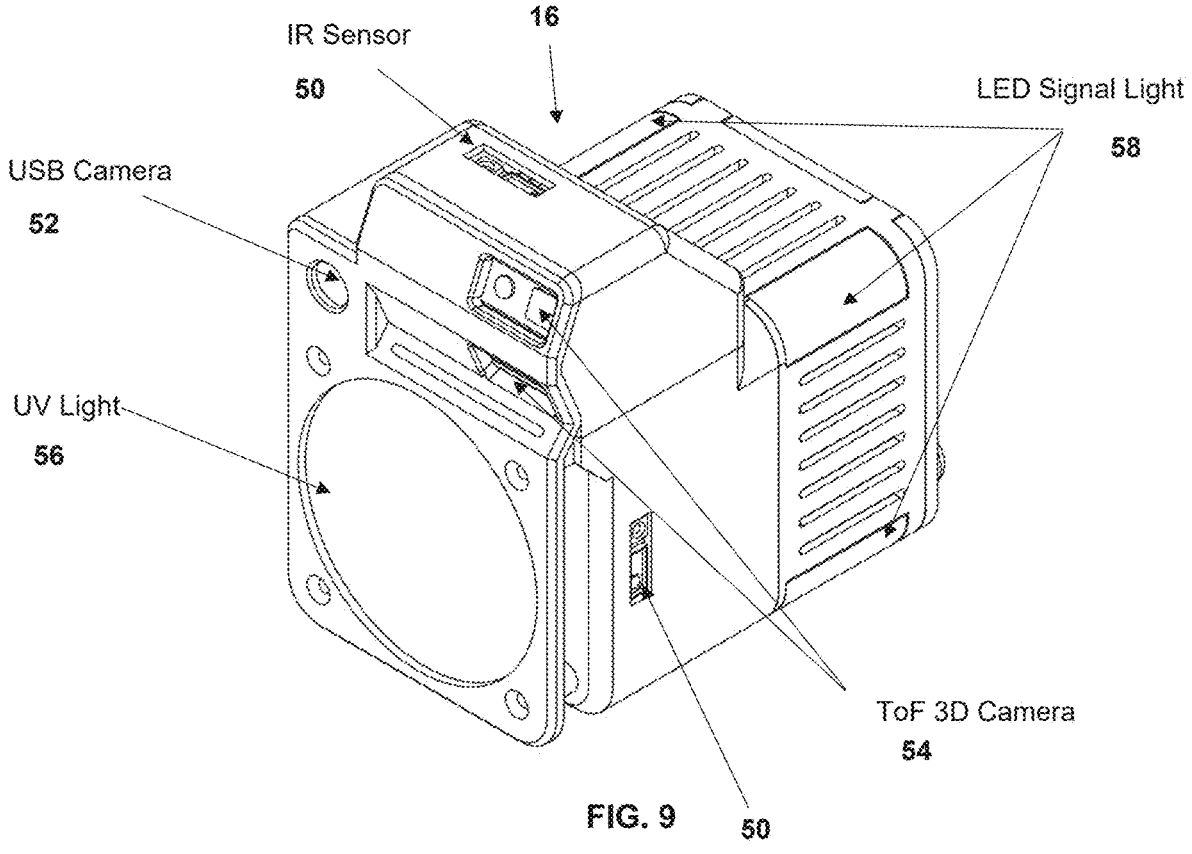
FIG. 9 is a perspective view of a UV-C light design for use with the present invention.

The UV-C light module, as shown in FIG. 9, is used to disinfect the target area. The module 16 is mounted on the robot manipulator arm 14. The robot arm brings the UV-C light module to within a few centimeters of the target surface. The model moves along the target surface at a fixed distance from it to ensure uniform disinfection performance. Users may remotely control the robot through remote PC 22, which is connected to the control 20 by WiFi, Bluetooth or some other communications link 21 as shown in FIG. 2. To assist the user control, a USB camera 52 and ToF 3D cameras 54 are installed to capture the real-time image of the working environment. The IR sensors are installed to protect the human while the disinfection process is going on.

As shown in FIG. 9, there are 4 IR sensors 50 with one installed on each side of the UV light module 16 to measure the distance between the UV light 56 and the object. When the distance becomes too close, a warning signal is sent and the operation of the robot is stopped. Four LED signal lights 58 are installed, one at each corner of the light module 16 to remind the user that the device is in operation. The 360 degrees USB camera 52 is installed at the front of the module to record the image. The image and video are sent while the robot is operating. The two ToF 3D cameras 54 are also installed at the front of the module 16 to collect 3D point clouds of the landscape and objects in front of the UV light module. A 100 W UV light 56 is installed on the front of the UV module to disinfect the area.

Figure 10:
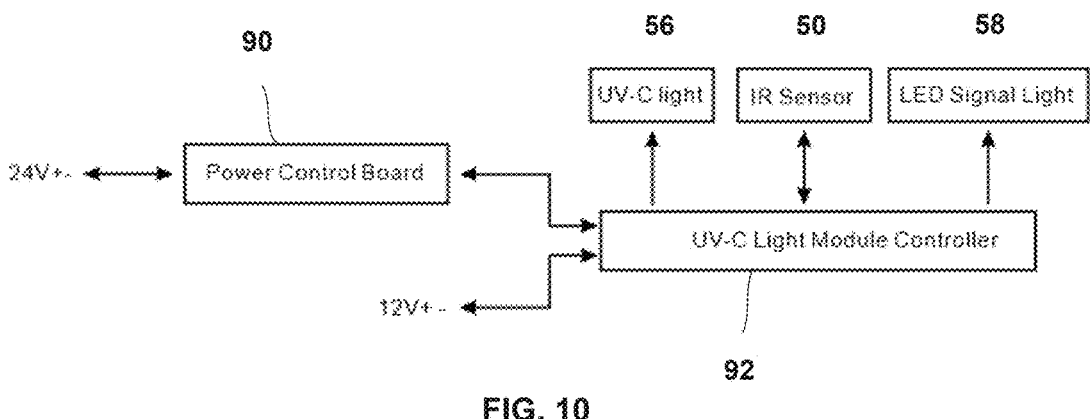
FIG. 10 is a block diagram of a control system for the UV-C light of FIG. 9.
Figure 11A:
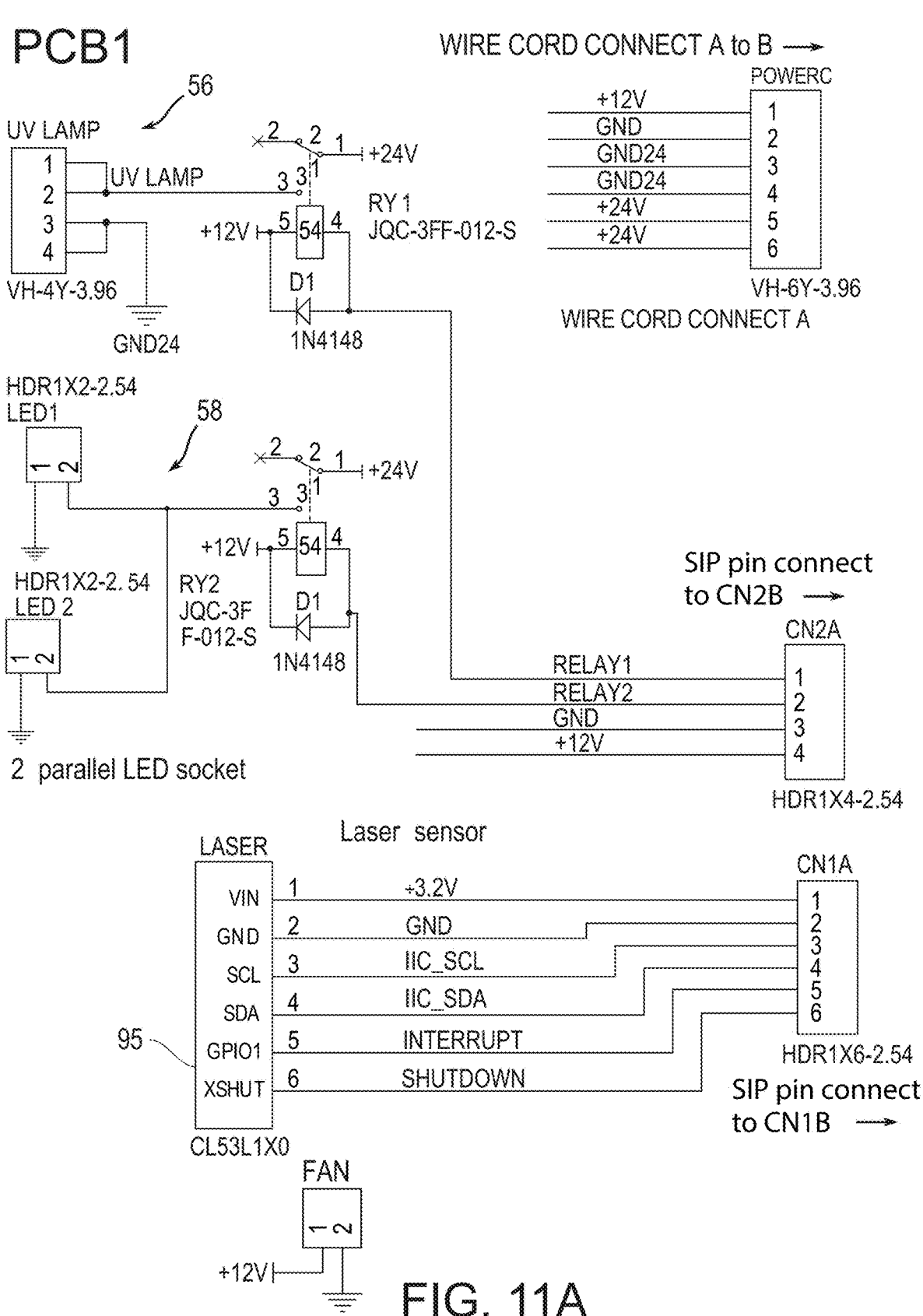
FIG. 11 is a schematic of the electronic system for the UV-C light of FIG. 9.
Figure 11B:
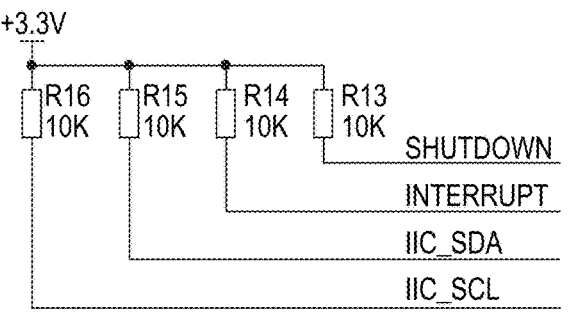
Figure 11B:
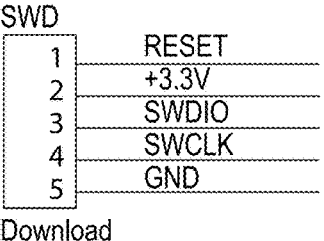
Figure 11B:
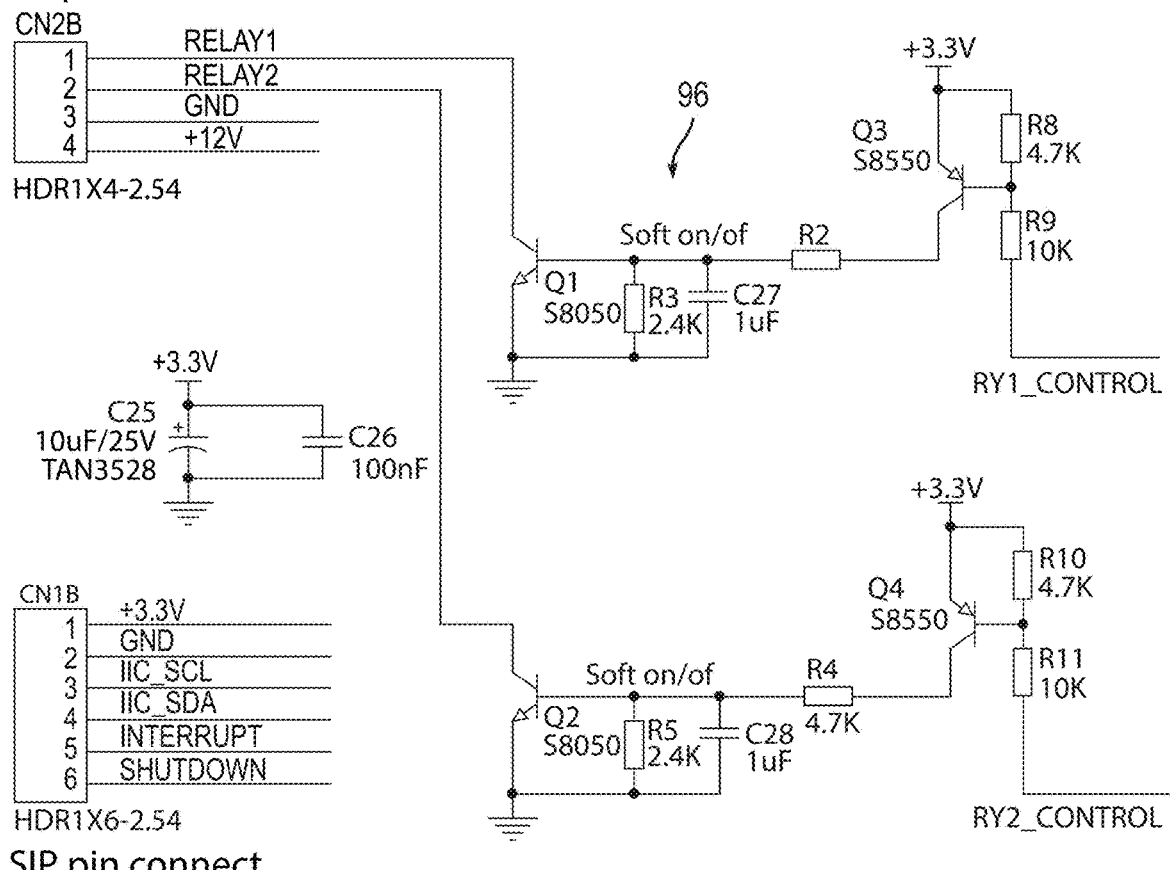
Figure 11C:
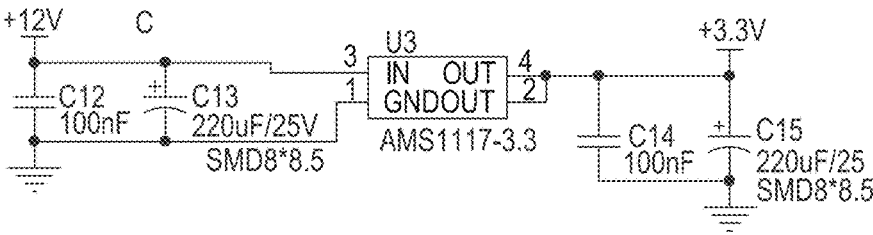
Figure 11C:
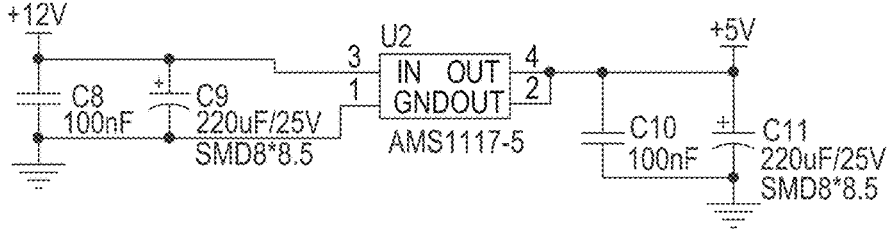
Figure 11C:
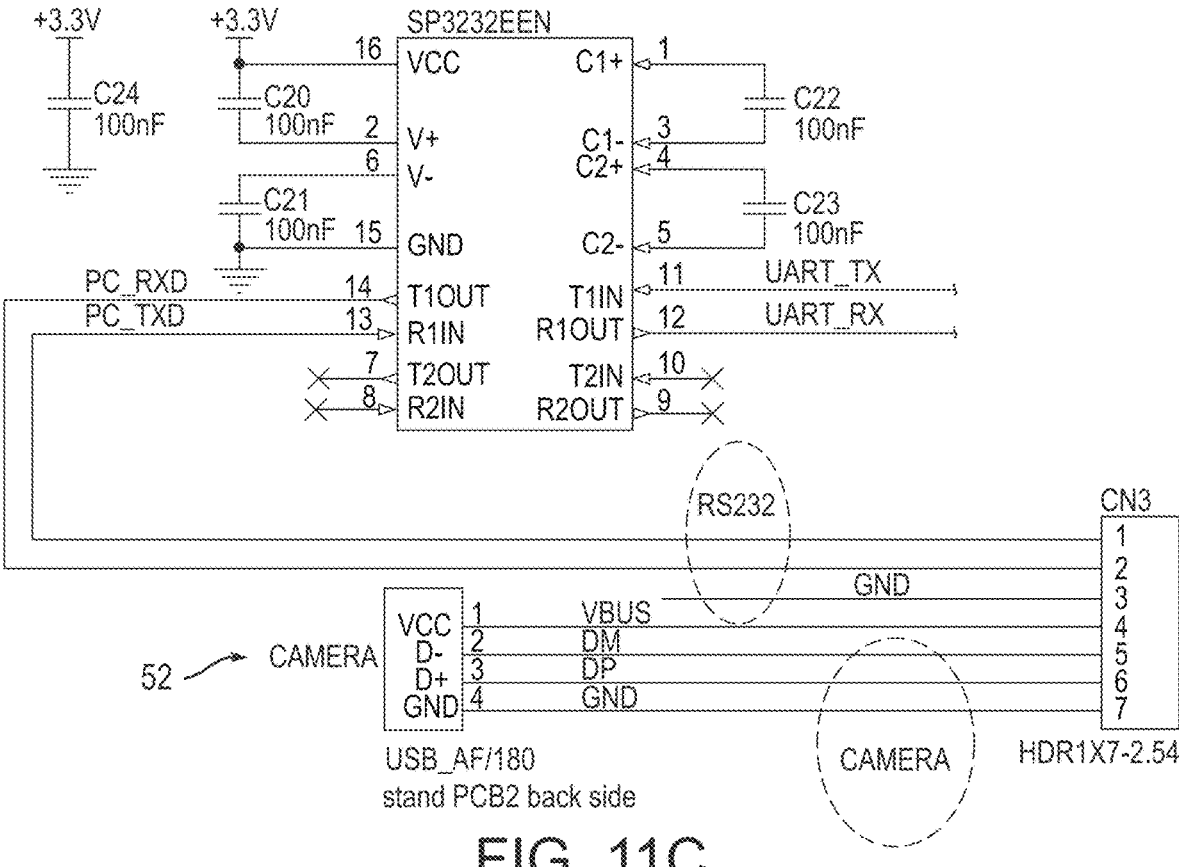
Figure 11D:
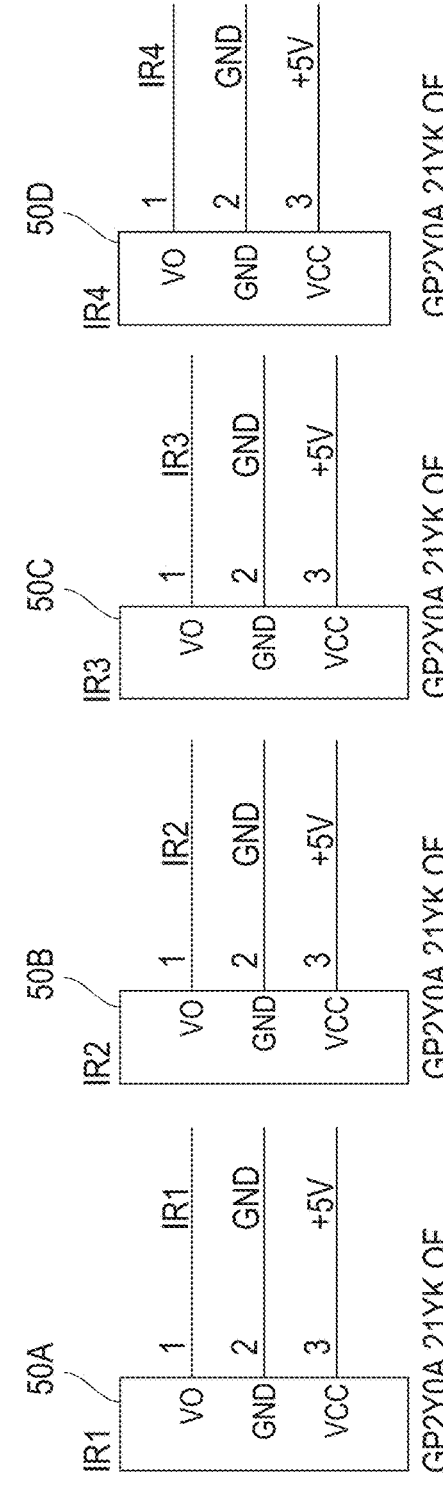
Figure 11E:
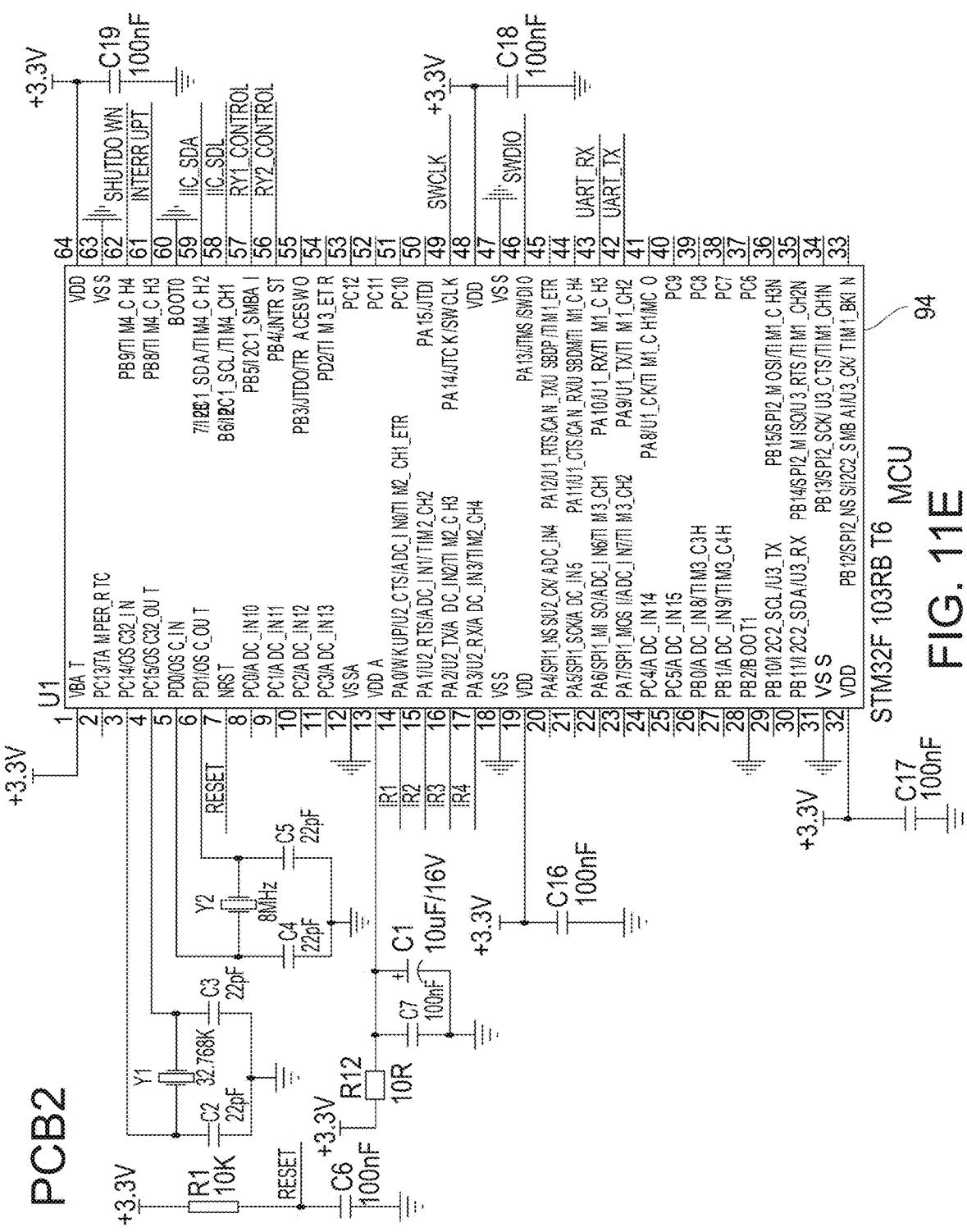
Figure 11F:
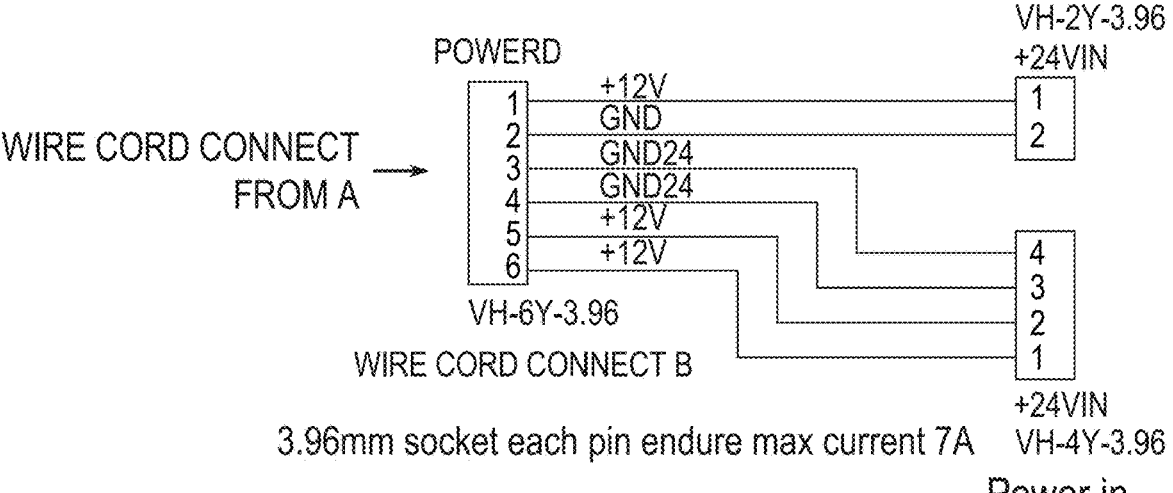

A block diagram of the control system of the UVC is shown in FIG. 10 where a power control board 90 is provided with 24-volt power. Board 90 is in communication with a UV-C light module controller 92. In addition, 12-volt power is delivered to controller 92. The controller activates the UV light 56 and the LED signal lights 58. Controller 62 also activates the IR Sensors 50 and receives the output from these sensors to control the distance of the UV light 16 from the surface to be cleaned.

A schematic of the control system of the UVC is shown in FIG. 11. At the heart of the control system is a micro-controller unit (MCU) 94. It is programmed to drive the 4 IR sensors 50A, 50B, 50C and 50D and receive their outputs from connector 95. Further, it operates the UV lamp or light 56 and the LED signal lights 58 through driver circuits 96. The output of USB camera 52 is provided to a USB connector.

Figure 12:
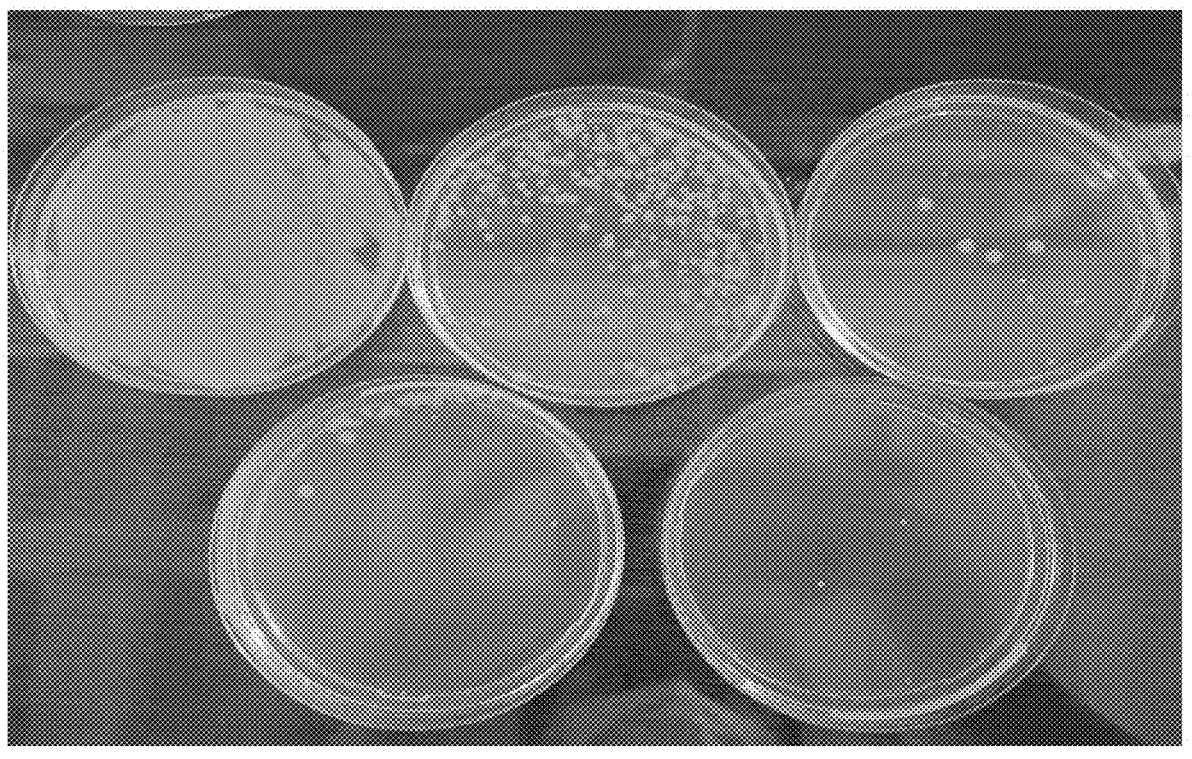
FIG. 12 is an image showing the results of disinfection of *E. coli* with the present invention for different distances and times.

Test were conducted with the disinfection robot of the present invention. The photograph of FIG. 12 shows the effect on 222 nm *E. coli*. In the control sample (upper left) no illumination was provided and the bacteria proliferated. Where the exposure time was 1 minute at a distance of 10 cm from the sample (upper center), there was a large reduction in the number of bacteria. When the exposure time was increased to 5 minutes (upper right) there was a drastic reduction in the number of bacteria over that when the exposure was only for 1 minute. Increasing the exposure to 3 minutes and 10 minutes (left and right lower, respectively) caused corresponding reductions in the bacteria.

FIG. 13 shows that beta-HCoV-OC43 results with continuous far-UVC exposure in occupied public locations at the current regulatory exposure limit (~3 mJ/cm2/hour) results in a 90% viral inactivation in 8 minutes, 95% in 11 minutes, 99% in 16 minutes and 99.9% inactivation in 25 minutes. Thus, while staying within current regulatory dose limits, a low-dose-rate of far-UVC exposure can safely provide a major reduction in the ambient level of airborne coronaviruses in occupied public locations. The photographs of FIG. 13 show alpha HCoV-229E in normal human lung MRC5 fibroblasts. FIG. 13A is for anti-human coronavirus spike glycoprotein without UV exposure. FIGS. 13B, C and D show DAPI fluorescent stain at exposures of 0.5 mJ/cm$^2$, 1 mJ/cm$^2$ and 2 mJ/cm$^2$, respectively.

FIG. 14A shows exposures of four cultures to UVC LED at 270 nm for 3000/0.5 min, 6000/1 min, 12000/2 min and 24000/3 min. FIG. 14B shows a graph of the number of colonies versus dosage in uJ/cm$^2$. This test shows that a 270 nm UVC: 1 min-6 mj/cm2 results in a 90%+disinfection efficiency. By comparison exposure with a LUMENIZER 222 nm lamp for 5 min caused a 90%+disinfection efficiency. Similarly, a test with a David J. Brenner 222 nm UVC for 8 min at 2 ml/cm$^2$ resulted in a 90%+disinfection efficiency Thus, the present invention produces the same disinfection efficiency as the prior art, but in less time.

As noted above, a disinfection motion plan, such as the trajectory of the robot End-Effector (E.E.) UVC light 16, can be described in the World Reference Frame ($\mathfrak{R}_{W.R.F}$) established in the global point cloud map. Such a disinfection plan is valid based on the assumption that the pose of the object being disinfected is static in the Global Reference Frame (G.R.F) where $T_W^L$, is static. Static objects include buttons on the walls, fixed bookshelves and desks. Then with pose estimation of the robot end effector in the global map($T_W^{EE}$), the pose control error can be calculated and gradually eliminated. However, this planning and control framework suffers in two respects.

Figure 15:
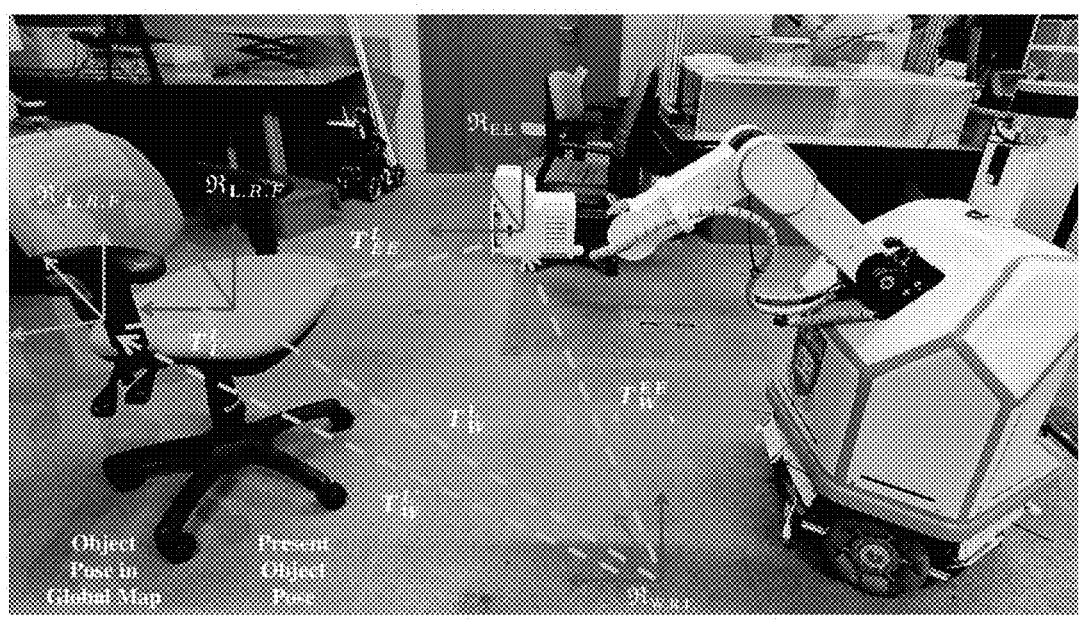
FIG. 15 is an illustration of reference frames and transforms for a movable object disinfection mobile manipulation task.

First, when encountering movable objects like chairs, the static object pose assumption cannot be valid since their pose ($T_W^L$) can vary from time to time in W.R.F. See FIG. 15, which illustrates the reference frames and transforms for a movable object disinfection mobile manipulation task. Therefore, the disinfection motion planning and control scheme in G.R.F. can cause collusions and/or unsatisfactory disinfection performance on movable objects. Second, the control error depends on the pose estimation of the robot end effector in the global map ($T_W^{EE}$), which can be unreliable when the environment changes, such as a new indoor furniture layout, compared with the one when the global map is established.

When considering the disinfection task with respect to a movable object, it becomes clear that the relative spatial relationship from the end effector (R_(E.E.)) to the latest object pose (R_(L.R.F)) is vital. Therefore, to meet the challenges of disinfecting movable objects, it is proposed as part of the present invention that the disinfection motion planning include a Local Reference Frame (R_(L.R.F)) which is attached to the movable object. The advantage of this is that it avoids motion re-planning each time the object pose is changed.

Additionally, the pose estimation reference is no longer the whole environment, just the object, which can reject the unreliable pose estimation caused by the environment changes. Two frameworks, one in vector space and one in non-vector space, are considered for accomplishing these innovative ideas, including reference frame conversion of the motion plan, error estimation and control in the local reference frame (R_(L.R.F)).

For the movable object, the vector space method uses the point cloud registration algorithm to output the transformation matrix in the vector space based on two different point clouds, one of the point clouds is the reference point cloud and the other one is the currently observed point cloud, called the "target point cloud." Both reference and target point cloud are described in the Local Reference Frame ($\mathfrak{R}_{L.R.F}$). The transformation matrix is acquired for converting from the reference point cloud to the target point cloud. Then robot can follow the given path and trajectory to finish the disinfection task and does not need to perform the motion planning again.

Figure 16:
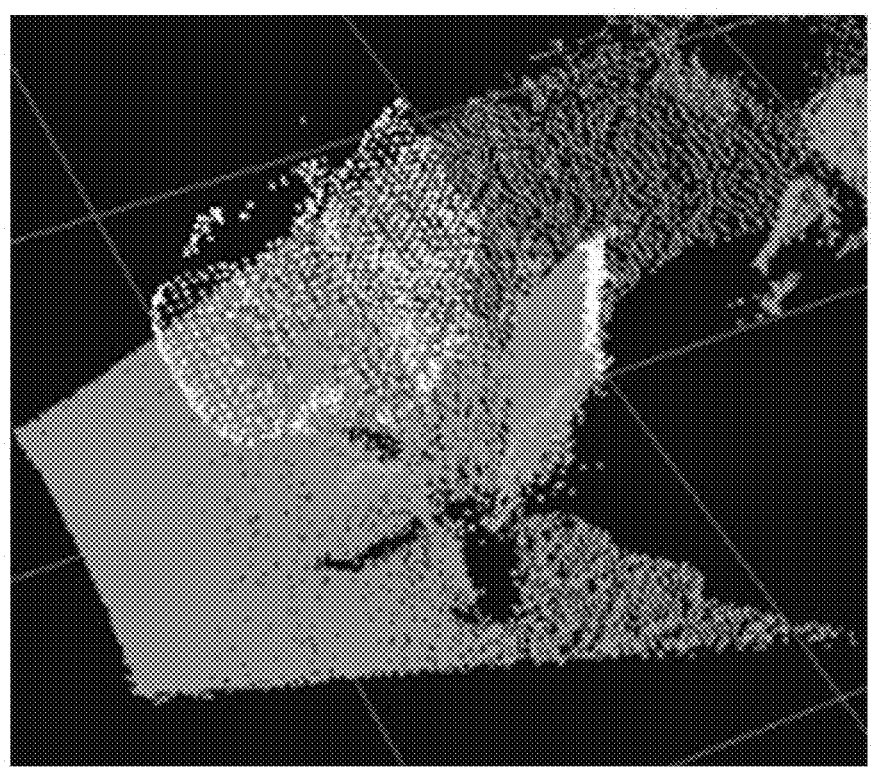
FIG. 16 is an illustration of point cloud registration according to an embodiment of the invention.

The vector space method needs to obtain the reference point cloud in advance. A relatively complete reference point cloud is usually collected, and it is described in the $\mathfrak{R}_{L.R.F}$. The end effector of the robot is provided with a 3D camera, which collects the target point cloud. The target point cloud is also described in the same coordinate frame with the reference point cloud. Moreover, when there are a reference point cloud and a target point cloud, the point cloud registration algorithm is used to calculate the transform matrix. First, the Point Feature Histogram (PFH) of the reference point cloud and the target point cloud need to be calculated. PFH features are not only related to the three-dimensional data of the coordinate axis, but they are also related to the surface normal. Then, the algorithm of Iterative Closest Point (ICP) is used to calculate the transformation relationship between these two different point clouds with their PFH features. The ICP algorithm will output a result with a score value. A lower score means a more accurate and confident result. FIG. 16 shows the reference point cloud, target point cloud and the output result. In the FIG. 16 the white cloud represents the reference point cloud, and the blue cloud represents the target point cloud. The orange point represents the result of the reference point cloud being transformed by the output transformation matrix.

After obtaining the transform relationship, the original motion planning that is attached to the movable object can be transferred to the target object by the output transform relationship. Therefore, the robot just needs to follow the given path and trajectory to disinfect the movable object without re-planning the entire path and trajectory for the

Figure 17:
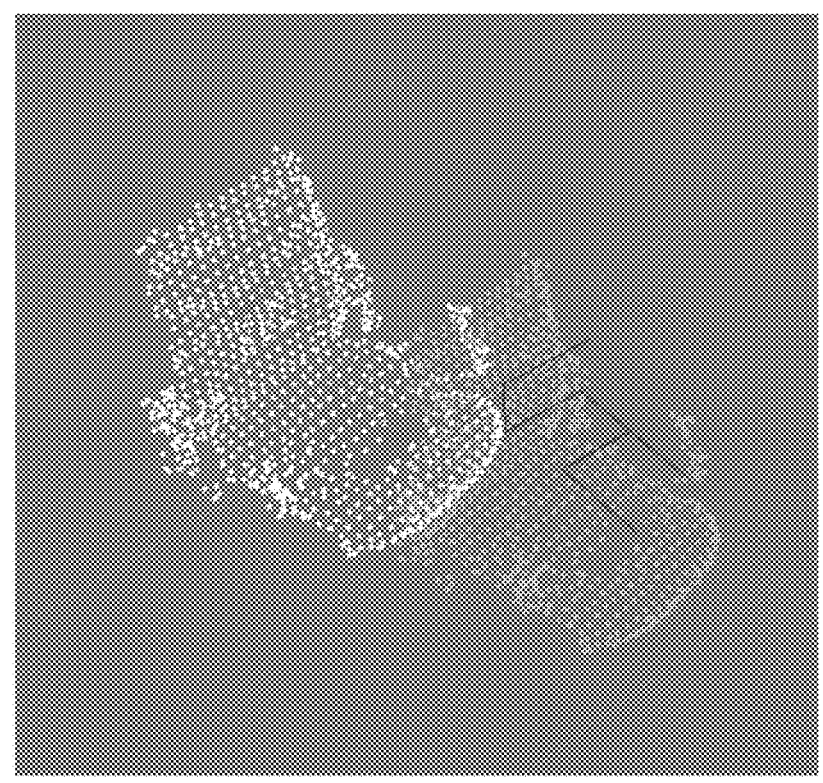
FIG. 17 is an illustration of path transformation according to an embodiment of the invention.

13 movable object. The path of motion planning shows in the FIG. 17. The green line represents the original path with the reference point cloud and the red line represents the target path with the target reference point cloud.

The idea of non-vector space planning and control framework involves using the movable object points set observed at $\mathfrak{R}_{E.E.}$ directly as the system state, which directly ensures the relative spatial relationship from the end effector to the object and largely omits feature extraction and vectorization computation cost in the vector-space algorithms, such as localization.

Figure 18:
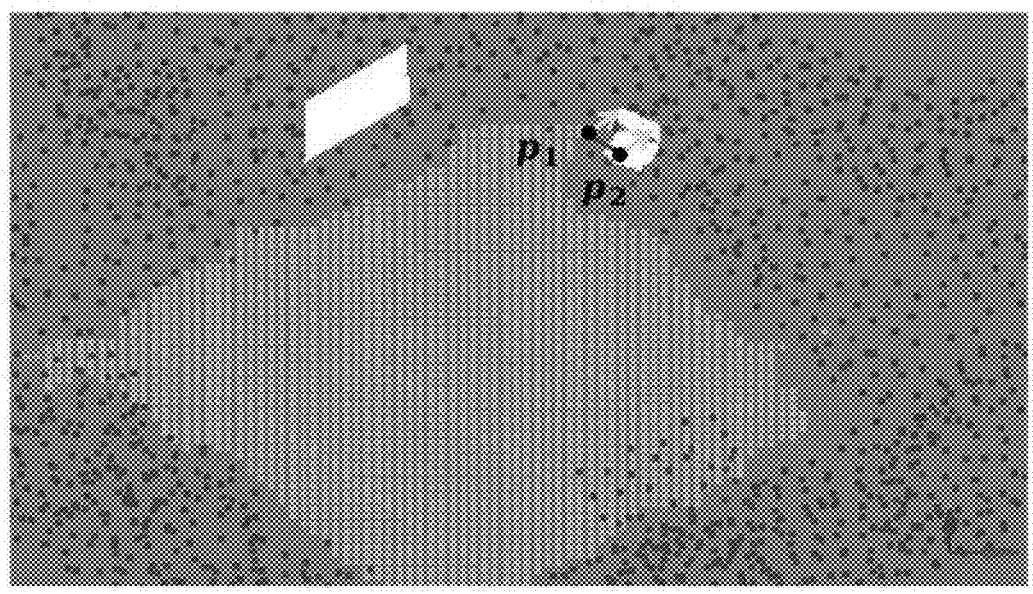
FIG. 18 illustrates a planned trajectory in vector space as two 3 dimensional points.

In motion plan conversion, the original vector space motion plan is a series of UVC light ($\mathfrak{R}_{E.E.}$) trajectory (time-varying pose, velocity, and acceleration vectors) in the $\mathfrak{R}_{W.R.F.}$ On the other hand, the motion plan is described by a series of continuously evolving sets, called "tube" in non-vector space. By having a virtual end effector ideally travel as described in the mentioned trajectory in a simulation environment (or the real end effector moves in real world), the 3D scanner on the end effector would simultaneously collect a series of points cloud of the object to be disinfected. Therefore the motion plan is converted from vectors described in $\mathfrak{R}_{W.R.F.}$ to sets observed in $\mathfrak{R}_{E.E.}$. A motion plan conversion example from vector-space line trajectory in $\mathfrak{R}_{W.R.F}$ (FIG. 18) to the non-vector space tube (first and last set in FIG. 19) is shown. The planned trajectory ($Y^d(t)/Y^d(s)$) in the vector space are shown in FIG. 18, where $p_1,p_2$ are two 3 dimensional points with a normal. In FIG. 19 the reference tube ($\hat{K}(t)/\hat{K}(s)$) in the non-vector space ($\hat{K}$) is a 3 dimensional points set.

As for the control process, the 3D scanner at the robot end effector obtains segmented points set K(t) of the movable object in real-time. Then a designed non-vector space controller converges the Wasserstein distance as the control error from K(t) to $\hat{K}$ by calculating the appropriate velocity of the end effector. During the control process, the movable object can still be moved and the robot end effector will robustly adopt such unexpected changes with the system shown in FIG. 20.

Figures 21A, 21B:
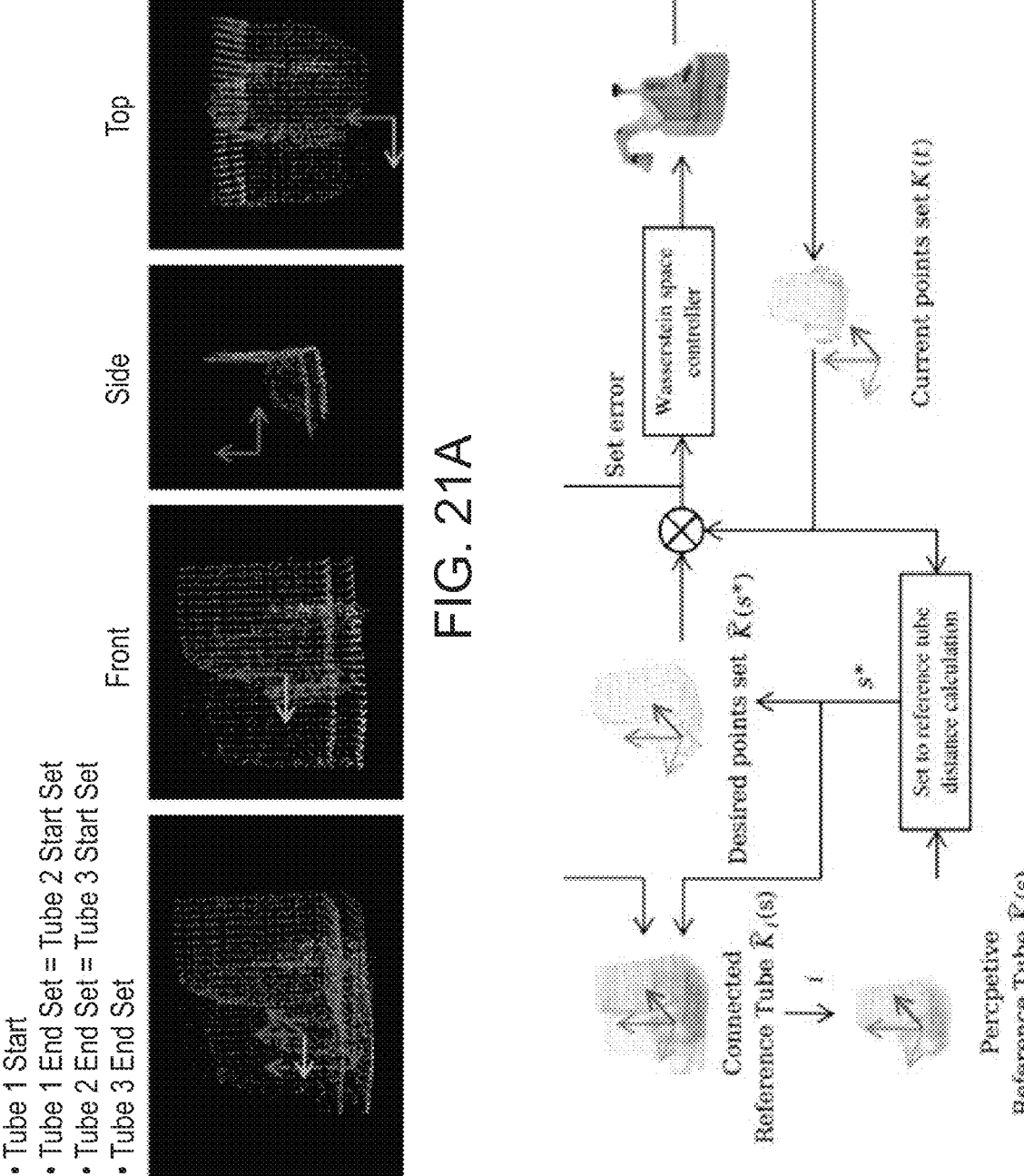
FIG. 21A shows three connected reference tubes in Wasserstein non-vector space as three 3-dimensional point sets and FIG. 21B is a block diagram of a multiple connected tubes following control framework in Wasserstein non-vector space.
Figure 22:
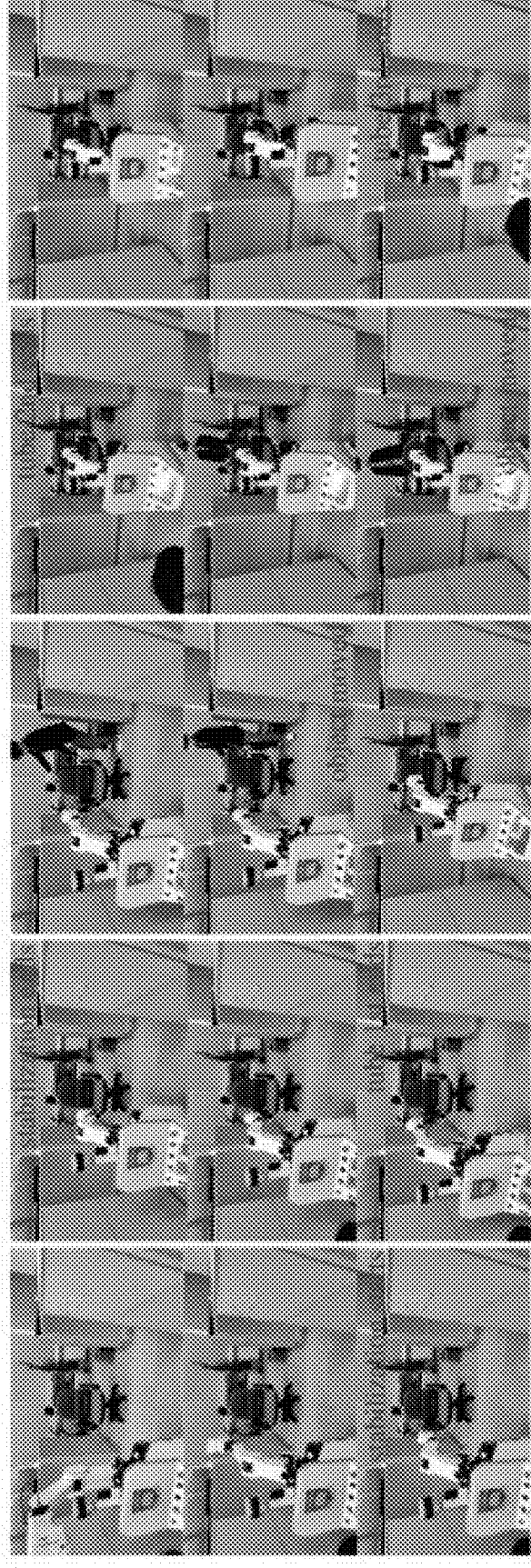
FIG. 22 is a series of photographs illustrating a non-vector space motion plan and control process with unexpected object movements.

In order to cover a larger object surface, a more complicated disinfection path can be expressed by more than one single tube in non-vector space. The snapshots in FIG. 21A show start and end sets in three connected reference tubes in $\mathfrak{R}_{E.E.}$ during a complete chair disinfection in Wasserstein non-vector space. The directions of three reference tubes are shown by arrows on one side, the front, the other side and the top. FIG. 21B shows multiple reference tubes following a control framework in Wasserstein non-vector space. In particular, the Current point set K(t) is received from the end effector. This set is combined with the Desired points set to $\hat{K}(s^*)$ to derive the set error that provides Wasserstein space control for the end effector. The Current points set is also provided to a distance calculator along with the Perceptive Reference Tube set $\hat{K}(s)$ to generate the Desired points set to $\hat{K}(s^*)$ used in the error calculation. In addition the Desired points set to $\hat{K}(s^*)$ and the set error are applied to the connected reference tube $\hat{K}_r(s)$ which in turn is used to derive the Perceptive Reference Tube set $\hat{K}(s)$ that is used in the distance calculator to derive the Desired points set to $\hat{K}(s^*)$ FIG. 22B shows the control processes with unexpected object movements. In particular, the series of images show the robot approaching a chair, the chair being moved, the robot finding the chair in its new location and the robot disinfecting the chair at the new location.

The vector space framework realizes high position control accuracy because it estimates the Euclidean transformation from the past scanned object to the present observed object once by point cloud registration algorithms. During the disinfection period, the end effector can approach the object closely with both an updated motion plan in R_(G.R.F) and closed-loop control in R_(G.R.F). However, the if the shape of the observed object is different from the reference object's shape, the point cloud registration will fail. Also, if the object is moved during the control process, the point cloud registration must be performed one more time.

The non-vector space framework shows better robust performance when there are partial observations of an interested object because these observations do not rely on the vector space transform precision of point cloud registration, and the unexpected movements of the object due to it's closed-loop control in R_(E.E.) throughout the whole disinfection process without a feature extraction process. Also, a disinfection plan can be used on multiple objects with similar shapes because the representation of sets error is Wasserstein distance, which can describe not only isometric transform but also shape difference. The drawback of non-vector space is that both the storage size and computation cost of creating the set are large. This is overcome by a point cloud voxel down-sampling filter and would be solved more efficiently by tools like compressive sensing.

Figure 23:
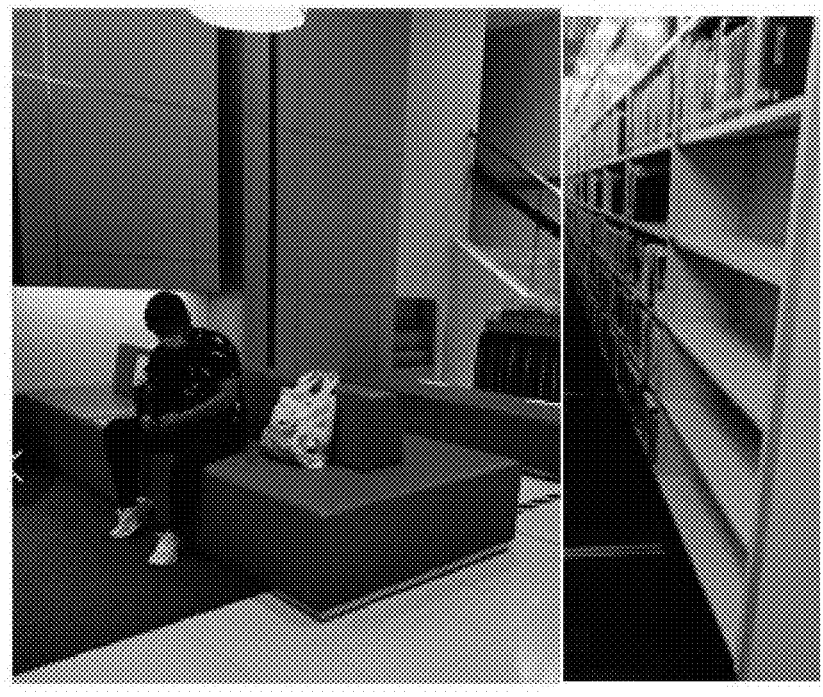
FIG. 23 shows photographs of an occupied object (sofa) and an empty container (shelves)

At the disinfection action level, there are still many situations, such as the object being occupied, an occupied object becoming free, an empty container and a full container as shown in FIG. 23. If the robot uses the same strategy and action for all these situations, it will a waste a lot of time and perform some meaningless operations. It may even sometimes do harm to the people who using the object. Thus, when the robot faces different situations, the robot should deal with them using different strategies and actions. For example, if there is a sofa and a person is sitting there at the same time, the robot should perform a skip action when the end effector is close to the person; If the robot disinfects the bookshelf, when the robot meets some empty space along the bookshelf, the robot should also perform a skip action to avoid disinfecting an empty space.

In facing the challenge of performing actions depending on the situations, the robot needs to detect the object state when it is performing disinfection tasks. After the occupancy or empty states are detected the system can rearrange its action to skip disinfection or postpone it. Because the system uses event-based detection in its framework, and the event-based motion planning allows rearrangement of the action without redoing the entire motion plan, its operation can be very efficient.

Figure 24:
FIG. 24 illustrates an object detection result on a chair according to the present invention.

The most important thing in this embodiment is to detect and classify different situations, which is realized by an algorithm called an "action online planner". According to the information from the RGB camera and 3D camera, the situations can be classified. Through the RGB camera, using the You Only Look Once (YOLO) algorithm can find different objects, such as chairs, sofa and human as shown in FIG. 24. Besides, the 3D camera, which that is located in the front of the end effector, can help to detect an empty or full container because the point cloud information shows different distances when the container is full and when it is empty. The action online planner collects all this sensor information in real-time and classifies different situations based on this information. After that, the action online planner will rearrange the action sequence, skipping the empty containers and occupied objects, and performing the disinfection action just on those free objects and full containers.

While the invention is explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A disinfection robot comprising: a mobile base with omni-directional wheels; a universally positionable manipulator with an end effector (E.E.); a UV lamp module attached to the E.E. of the manipulator that includes a UV disinfection lamp and a ranging module using sensors to detect the distance of the lamp from a surface to be disinfected; and an electronic control system for planning a path for the base to move about a space and the UV disinfection lamp to be moved over surfaces in the space based on information from the sensors and for controlling the directional wheels of the base and the movement of the manipulator so as to cause the UV disinfection lamp to follow the path and disinfect the space; wherein the electronic control system includes a path processor configured to plan a path by executing instructions according to an object perceptive local planner method comprising the steps of: segmenting X(t) segments from a real-time point cloud; segmenting $X_{ref}f(s)$ segments from a global map as the E.E.'s desired path; using the selected segments X(t) with a point cloud sliced Wasserstein based perceptive motion local planner to map a UV desired path compared to an actual UV path; updating the comparison; and updating a speed profile of the E.E. along a geodesics path, whereby an optimal transport path from X(t) to $X_{ref}f(s)$ is established.

2. The disinfection robot according to claim 1 wherein the ranging module includes a multi-line laser scanner and a 360 degrees camera.

3. The disinfection robot according to claim 2 wherein the ranging module is a LIDAR system.

4. The disinfection robot according to claim 1 further including a remote processor with a transceiver and a transceiver connected to the electronic control circuit so the remote processor and electronic control circuit can communicate over a transmission link so that a user can control the robot remotely.

5. The disinfection robot according to claim 4 wherein the remote processor and the electronic control circuit communicate over a WiFi transmission link.

6. The disinfection robot according to claim 1 wherein the universally positionable manipulator has 3 rotational joints, which are located in three XYZ joint frames, and the mobile base is located in a separate XYZ frame.

7. The disinfection robot according to claim 1 wherein the electronic control system acquires from the sensors a velocity, acceleration, position and time in task space according to known initial and end points, and generates a plan for a trajectory to control the E.E. so it follows this trajectory.

8. The disinfection robot according to claim 7 wherein the trajectory is divided into three sections: third-order, fifth-order and third-order trajectories; and after performing the third-order, fifth-order and third-order trajectories in the planner, a pose of each point in task space is transformed into joint space to control the robot's joint through an inverse kinematics and a Jacobian matrix so that commands can be published to control the joints based on the position and velocity, where the velocity and position correspond to a specific time.

9. The disinfection robot according to claim 1 wherein the electronic control system contains a feedforward part and a feedback part and a controller for the manipulator, wherein the feedforward part is acquired through a Dynamics model to compute torque in the controller and the feedback part is the position and velocity, wherein based on a position and velocity error, a position loop and a velocity loop are constructed, wherein a feedforward of torque is combined with the position loop and velocity loop to calculate a decoupling output, a controller output is a controller torque output whose value satisfies a requirement of an entire robot system in order to realize a target, including mutual influence between each joint; and wherein the controller torque output is provided to a driver for the manipulator, and the driver generates current to make manipulator motors operate according to the corresponding controller torque output.

10. The disinfection robot according to claim 1 wherein the comparisons are updated at a rate of 10 Hz and the speed profile is updated at a rate of 50 Hz.

11. The disinfection robot according to claim 1 further including a time-of-flight (ToF) camera attached to the UV light module at the E.E. and a Light Detection and Ranging (LiDAR) device on the robot base, and wherein the electronic control system includes a path processor configured to plan a path by executing instructions according to the method of planning the path comprises the steps of: receiving a present image, l(t), a present point cloud X(t) and camera_intrinsics.yaml & camera_toflf.launch signals from the robot at a present point cloud segmentation processor; producing at the present point cloud segmentation processor a visual cone in the local frame and $X_{seg}(t)$, which is delivered to a sliced perceptive object tracker; receiving UVdesired.txt, Map.ply and pnum(s) at a.reference point cloud generator, which in turn generates $X'_{seg}(s)$, which is applied to the sliced perceptive object tracker along with an E.E. State and E.E. constraints, wherein the E.E. constraints come from joint dynamic constraints and environmental information after passing through a dynamics module; causing the sliced perceptive object tracker to engage in trajectory planning with dynamic constraints on a geodesics path and Wasserstein barycentre as intersections from X to X,' wherein the sliced perceptive object tracker produces as an output a point cloud registration (based on sliced Wasserstein distance); passing the point cloud registration to a point cloud sliced Wasserstein-based perceptive motion local planner, wherein the planner has its output tf: from/UV to/UV desired directed to the reference point cloud generator as an input along with $X'_{seg}(s)$ and LIDAR_FoV.yami; applying a second output of the planner to a calculation block which engages in e_calculation (known/map to/UV), which provides the input Pnum(s) to the reference point cloud generator; and applying an output p(T) from the sliced perceptive object tracker to a kinematics unit to create q(t), which is directed to the robot, and which in turn provides the present image and present point cloud applied to the present point cloud segmentation unit, whereby global localization is used as an initial condition, then it mainly compares reference point cloud and present point cloud in the end effector frame (E.E.F.) of the mobile manipulator based on Wasserstein distance, and then outputs rigid transformation between them at a low frequency and desired velocity along the optimal path of the E.E. at a high frequency.

12. The disinfection robot according to claim 1 for conducting a disinfection task with respect to a movable object, further including a 3D camera on the E.E. of the robot, and wherein the electronic control system includes a disinfection motion planning module with a Local Reference Frame (R_(L.R.F)) attached to the movable object, which planning module includes a plan processor configured to execute instructions to carry out the steps of' obtaining a reference point cloud in advance; collecting a target point cloud with the 3D camera; utilizing a vector space with a point cloud registration algorithm to output a transformation matrix in the vector space based on the reference point cloud and the target point cloud, wherein the transformation matrix is acquired for converting from the reference point cloud to the target point cloud; transferring the original motion planning that is attached to the movable object to the target object according to the output transformation matrix; and causing the robot E.E. to follow a given path and trajectory to finish the disinfection of the movable object without being required to perform additional motion planning for the entire path and trajectory.

13. The disinfection robot according to claim 12 wherein the point cloud registration algorithm comprises the steps of: calculating a Point Feature Histogram (PFH) of the reference point cloud and the target point cloud, wherein the PFH features are related to three-dimensional data of the coordinate axis and the surface normal; and calculating a transformation relationship between the two different point clouds with their PFH features using the algorithm of Iterative Closest Point (ICP), which outputs a result with a score value where lower score means a more accurate and confident result.

14. The disinfection robot according to claim 1 for conducting a disinfection task with respect to a movable object, further including a 3D camera on the E.E. of the robot, and wherein the electronic control system includes a disinfection motion planning module which includes a plan processor configured to execute instructions to carry out the steps of using a movable object points set observed at an end effector reference, $\mathfrak{R}_{E.E.}$ directly as the system state, which directly ensures the relative spatial relationship from the E.E. to the object; wherein the motion plan is a series of continuously evolving sets or "tube" in non-vector space generated by (a) expert demonstration in $\mathfrak{R}_{E.E.}$ by joystick E.E. control or (b) convention from vector space trajectory in world reference frame $\mathfrak{R}_{W.R.F.}$, and the plan processor of the module executes instructions to carry out the steps of: (a) having the 3D scanner on the E.E. simultaneously collect a series of cloud points of the object to be disinfected while the E.E. is controlled by an expert in a disinfection demonstration process; (b) converting the motion plan from vectors described in $\mathfrak{R}_{W.R.F.}$ to sets observed in $\mathfrak{R}_{E.E.}$—to the non-vector space tube while a virtual E.E. with a ToF LiDAR FoV culling point cloud collector travels in a described trajectory in a simulation environment; having the 3D scanner at the robot E.E. obtain segmented points set K(t) of the movable object in real-time; using a designed non-vector space controller to converge the Wasserstein distance as the control error from K(t) to K with theoretical and experimentally proven exponential stable by calculating the appropriate velocity of the E.E.; and causing the robot E.E. to maintain a certain relative spatial relationship to the movable object and to impose effective UVC dosage without being required to perform additional motion planning for the entire path and trajectory.

* * * * *